(12) United States Patent
Welch et al.

(10) Patent No.: US 10,647,732 B2
(45) Date of Patent: May 12, 2020

(54) N-ANNULATED PERYLENE DIIMIDE DIMERS WITH ACTIVE PYRROLIC N—H BONDS

(71) Applicant: UTI Limited Partnership, Calgary (CA)

(72) Inventors: Gregory C. Welch, Calgary (CA); Arthur D. Hendsbee, Calgary (CA)

(73) Assignee: UTI Limited Partnership, Calgary, Alberta (CA)

( * ) Notice: Subject to any disclaimer, the term of this patent is extended or adjusted under 35 U.S.C. 154(b) by 93 days.

(21) Appl. No.: 15/866,376

(22) Filed: Jan. 9, 2018

(65) Prior Publication Data

US 2019/0211035 A1   Jul. 11, 2019

(51) Int. Cl.

| C07D 519/00 | (2006.01) |
|---|---|
| C08G 61/12 | (2006.01) |
| C08J 5/18 | (2006.01) |
| H01L 51/00 | (2006.01) |
| C08G 73/10 | (2006.01) |
| H01M 8/18 | (2006.01) |
| H01L 51/42 | (2006.01) |
| H01L 51/05 | (2006.01) |

(52) U.S. Cl.
CPC ......... *C07D 519/00* (2013.01); *C08G 61/124* (2013.01); *C08G 73/1003* (2013.01); *C08J 5/18* (2013.01); *H01L 51/0053* (2013.01); *H01L 51/0058* (2013.01); *H01L 51/0072* (2013.01); *H01L 51/0073* (2013.01); *C08G 2261/122* (2013.01); *C08G 2261/148* (2013.01); *C08G 2261/149* (2013.01); *C08G 2261/1424* (2013.01); *C08G 2261/226* (2013.01); *C08G 2261/3241* (2013.01); *C08G 2261/344* (2013.01); *C08G 2261/80* (2013.01); *C08G 2261/90* (2013.01); *C08G 2261/91* (2013.01); *C08G 2261/92* (2013.01); *C08J 2365/00* (2013.01); *H01L 51/0007* (2013.01); *H01L 51/0512* (2013.01); *H01L 51/42* (2013.01); *H01M 8/188* (2013.01)

(58) Field of Classification Search
CPC . C07D 519/00; C08G 61/124; H01L 51/0072; C08J 2365/00
See application file for complete search history.

(56) References Cited

U.S. PATENT DOCUMENTS

| 9,865,819 B2 | 1/2018 | Hendsbee et al. |
| 2017/0352812 A1 | 12/2017 | Hendsbee et al. |

FOREIGN PATENT DOCUMENTS

| CN | 104892629 A | 9/2015 |
| WO | WO 2016/016498 A1 | 2/2016 |

OTHER PUBLICATIONS

Hendsbee (Chem. Mater. 2016, 18:7098-7109).*
Anthony (2011) "Small-Molecule, Nonfullerene Acceptors for Polymer Bulk Heterojunction Organic Photovoltaics," Chem. Mater. 23:583-590.
Anthony et al. (2002) "A Road Map to Stable, Soluble, Easily Crystallized Pentacene Derivatives," Org. Lett. 4(1):15-18.
Bredas (Sep. 19, 2013) "Mind the Gap!" Mater. Horiz. 1:17-19.
Burke et al. (May 15, 2013) "Green Chemistry for Organic Solar Cells," Energy Environ. Sci. 6:2053-2066.
Cann et al. (Nov. 2017) "Spectroscopic Engineering toward Near-Infrared Absorption of Materials Containing Perylene Diimide," ChemPlusChem. 82(11):1359-1364.
Cardona et al. (2011) "Electrochemical Considerations for Determining Absolute Frontier Orbital Energy Levels of Conjugated Polymers for Solar Cell Applications," Adv. Mater. 23:2367-2371.
Chang et al. (Oct. 2013) "Correlating Dilute Solvent Interactions to Morphology and OPV Device Performance," Org. Electron. 14:2431-2443.
Chen et al. (2010) "1,7-Dinitroperylene bisimides: facile synthesis and characterization as n-type organic semiconductors," Tetrahedron Lett. 51(45):5959-5963.
Chen et al. (Dec. 8, 2014) "Highly Soluble Monoamino-Substituted Perylene Tetracarboxylic Dianhydrides: Synthesis, Optical and Electrochemical Properties," Int. J. Mol. Sci. 15(12): 22642-22660.
Chochos et al. (Jan. 18, 2013) "Rational Design on N-Type Organic Materials for High Performance Organic Photovoltaics," RSC Adv. 3:7160-7181.
Ding et al. (2012) "Alkylene-Chain Effect on Microwire Growth and Crystal Packing of π-Moieties," Chem. Mater. 24:1944-1949.
Eftaiha et al. (2014) "Recent Advances of Non Fullerene, Small Molecular Acceptors for Solution Processed Bulk Heterojunction Solar Cells," J. Mater. Chem. A. 2:1201-1213.
Fitzner et al. (2012) "Interrelation between Crystal Packing and Small-Molecule Organic Solar Cell Performance," Adv. Mater. 24:675-680.
Forrest (2004) "The Path to Ubiquitous and Low-Cost Organic Electronic Appliances on Plastic," Nature. 428:911-918.
Kim et al. (2012) "Influence of Structural Variation on the Solid-State Properties of Diketopyrrolopyrrole-Based Oligophenylenethiophenes: Single-Crystal Structures, Thermal Properties, Optical Bandgaps, Energy Levels, Film Morphology, and Hole Mobility," Chem. Mater. 24:1699-1709.
Li et al. (Feb. 29, 2012) "Polymer Solar Cells," Nat. Photonics. 6:153-161.
Liao et al. (Aug. 13, 2013) "Fullerene Derivative-Doped Zinc Oxide Nanofilm as the Cathode of Inverted Polymer Solar Cells with Low-Bandgap Polymer (PTB7-Th) for High Performance," Adv. Mater. 25:4766-4771.
Liao et al. (Sep. 2013) "Additives for Morphology Control in High-Efficiency Organic Solar Cells," Mater. Today. 16:326-336.

(Continued)

*Primary Examiner* — Kuo Liang Peng
(74) *Attorney, Agent, or Firm* — Leydig, Voit & Mayer, Ltd.

(57) ABSTRACT

PDI derivatives useful as opto-electronically active materials or for the synthesis of such materials. Certain compounds herein function as efficient electron acceptors and are useful as electron active components of electronic devices.

21 Claims, 7 Drawing Sheets

(56) References Cited

OTHER PUBLICATIONS

Lin et al. (Apr. 10, 2014) "Non-Fullerene Acceptors for Organic Photovoltaics: An Emerging Horizon," Mater. Horiz. 1:470-488.
Liu et al. (Oct. 11, 2016) "Non-fullerene small molecule acceptors based on perylene diimides," J. Mater. Chem. A. 4:17604-17622.
Lu et al. (Mar. 26, 2014) "Understanding Low Bandgap Polymer PTB7 and Optimizing Polymer Solar Cells Based on it," Adv. Mater. 26:4413-4430.
Marrocchi et al. (Jan. 12, 2016) "Current Methodologies for a Sustainable Approach to [Capital Pi]-Conjugated Organic Semiconductors," Energy Environ. Sci. 9:763-786.
McAfee et al. (Feb. 2017) "Applying direct heteroarylation synthesis to evaluate organic dyes as the core component in POI-based molecular materials for fullerene-free organic solar cells," J. Mater. Chem. A. 5:11623-116.
McAfee et al. (Jun. 2017) "A non-fullerene acceptor with a diagnostic morphological handle for streamlined screening of donor materials in organic solar cells," J. Mater. Chem. A. 5:16907-16913.
McAfee et al. (Jun. 26, 2015) "Key Components to the Recent Performance Increases of Solution Processed Non-Fullerene Small Molecule Acceptors," J. Mater. Chem. A. 3:16393-16408.
Namepetra et al. (Mar. 31, 2016) "Understanding the Morphology of Solution Processed Fullerene-Free Small Molecule Bulk Heterojunction Blends," Phys. Chem. Chem. Phys. 18:12476-12485.
Roncali et al. (Mar. 31, 2014) "Molecular Materials for Organic Photovoltaics: Small Is Beautiful," Adv. Mater. 26:3821-3838.
Su et al. (2012) "Organic Photovoltaics," Mater. Today. 15(12):554-562.
Zhan et al. (Mar. 8, 2016) "More than Conformational 'Twisting' or 'Coplanarity': Molecular Strategies for Designing High-Efficiency Nonfullerene Organic Solar Cells," Chem. Mater. 28:1948-1964.
Zhan et al. (Oct. 8, 2015) "New Advances in Non-Fullerene Acceptor Based Organic Solar Cells," RSC Adv. 5:93002-93026.
Zhang et al. (Dec. 10, 2014) "Non-Fullerene Organic Solar Cells with 6.1% Efficiency through Fine-Tuning Parameters of the Film-Forming Process," Chem. Mater. 27:166-173.
Zhang et al. (Jun. 1, 2016) "High-Efficiency Nonfullerene Polymer Solar Cell Enabling by Integration of Film-Morphology Optimization, Donor Selection, and Interfacial Engineering," ACS Appl. Mater. Interfaces. 8:15415-15421.
Zhao et al. (Jan. 20, 2016) "Electron Acceptors Based on α-Substituted Perylene Diimide (PDI) for Organic Solar Cells," Chem. Mater. 28:1139-1146.
Zhao et al. (Oct. 30, 2014) "High-Efficiency Non-Fullerene Organic Solar Cells Enabled by a Difluorobenzothiadiazole-Based Donor Polymer Combined with a Properly Matched Small Molecule Acceptor," Energy Environ. Sci. 8:520-525.
Zhong et al. (2015) "Molecular helices as electron acceptors in high-performance bulk heterojunction solar cells," Nat. Commun. 6:8242.
Acikbas et al. (Feb. 2016) "Optical Characterization of an N, N'-Dicyclohexyl-3, 4:9, 10-Perylene bis(Dicarboximide) Langmuir-Blodgett Film for the Determination of Volatile Organic Compounds," Anal. Lett. 46(16):2573-2586.
Cann et al. (Feb. 2017) "N-Annulated perylene diimide dimers: acetylene linkers as a strategy for controlling structural conformation and the impact on physical, electronic, optical and photovoltaic properties," J. Materials Chem. C. 5:2017-2083.
Centore et al. (2012) "Perylene Diimides Functionalized with N-Thiadiazole Substituents: Synthesis and Electronic Properties in OFET Devices," Org. Electron. 13:2083-2093.
Chen et al. (2007) "Photoluminescence and Conductivity of Self-Assembled π-π Stacks of Perylene Bisimide Dyes," Chem. Eur. J. 13:436-449.
Chen et al. (Apr. 2015) "A Perylene Diimide (PDI)-Based Small Molecule with Tetrahedral Configuration as a Non-Fullerene Acceptor for Organic Solar Cells," J. Mater. Chem. C. 3:4698-4705.

Dayneko et al. (Published Online Dec. 21, 2016) "Fullerene-free polymer solar cells processed from non-halogenated solvents in air with PCE of 4.8%," Chem Commun. 53:1164-1167.
Demmig et al. (1988) "Leichtlösliche, Lichtechte Perylen-Fluoreszenzfarbstoffe," Chem. Ber. 121:225-230; Eng. Title: "Very Soluble and Photostable Perylene Fluorescent Dyes." In German with English Abstract.
Doval et al. (2012) "Amphiphilic Dynamic NDI and PDI Probes: Imaging Microdomains in Giant Unilamellar Vesicles," Org. Biomol. Chem. 10:6087-6093.
Dwivedi et al. (Nov. 2014) "Assembly Modulation of PDI Derivative as a Supramolecular Fluorescence Switching Probe for Detection of Cationic Surfactant and Metal Ions in Aqueous Media," ACS Appl. Mater. Interfaces. 6:21369-21379.
Feng et al. (2012) "A Turn-on Fluorescent Sensor for Pyrophosphate Based on the Disassembly of Cu2+-Mediated Perylene Diimide Aggregates," ACS Appl. Mater. Interfaces. 4:614-618.
Fernandez-Lazaro et al. (May 2016) "Perylenediimides as Non-Fullerene Acceptors in Bulk-Heterojunction Solar Cells (BHJSCs)," J. Mater. Chem. A. 4:9336-9346.
Freeman et al. (2005) "Triphenylphosphine-Mediated Reductive Cyclization of 2-Nitrobiphenyls: A Practical and Convenient Synthesis of Carbazoles," J. Org. Chem. 70:5014-5019.
Hariharan et al. (Published Online Nov. 20, 2015) "Perylene Diimide Based Fluorescent Dyes for Selective Sensing of Nitroaromatic Compounds: Selective Sensing in Aqueous Medium Across Wide pH Range," J. Fluoresc. 26:395-401.
Hartnett et al. (Oct. 2014) "Slip-Stacked Perylenediimides as an Alternative Strategy for High Efficiency Nonfullerene Acceptors in Organic Photovoltaics," J. Am. Chem. Soc. 136:16345-16356.
Hendsbee (Jun. 2017) "Conjugated Organic Molecules Containing Imide Functional Groups for Organic Electronics," Ph.D. Thesis. University of Calgary, Calgary, Alberta, Canada.
Hendsbee et al. (Jan. 2014) "Electron Deficient Diketopyrrolopyrrole Dyes for Organic Electronics: Synthesis by Direct Arylation, Optoelectronic Characterization, and Charge Carrier Mobility," J. Mater. Chem. A. 2(12):4198-4207.
Hendsbee et al. (Jul. 2105) "Phthalimide-Based [Small Pi]-Conjugated Small Molecules with Tailored Electronic Energy Levels for Use as Acceptors in Organic Solar Cells," J. Mater. Chem. C. 3:8904-8915.
Hendsbee et al. (Mar. 2017) "N-annulated perylene diimide dimers: the effect of thiophene bridges on physical, electronic, optical, and photovoltaic properties," Sustainable Energy & Fuels. 1:1137-1147.
Hendsbee et al. (Sep. 2016) "Synthesis, Self-Assembly, and Solar Cell Performance of N-Annulated Perylene Diimide Non-Fullerene Acceptors," Chem. Mater. 28:7098-7109.
Huang et al. (Jun. 2014) "Probing the Sensory Property of Perylenediimide Derivatives in Hydrazine Gas: Core-Substituted Aromatic Group Effect," ACS Appl. Mater. Interfaces. 6:9307-9313.
Hüttner et al. (2008) "N-Type Organic Field Effect Transistors from Perylene Bisimide Block Copolymers and Homopolymers," Appl. Phys. Lett. 92:093302.
Jiang et al. (Published Online Oct. 30, 2013) "Bay-Linked Perylene Bisimides as Promising Non-Fullerene Acceptors for Organic Solar Cells," Chem. Commun. 50:1024-1026.
Kozma et al. (2013) "Perylene Diimides Based Materials for Organic Solar Cells," Dyes Pigm. 98:160-179.
Langhals et al. (2000) "Novel Fluorescent Dyes by the Extension of the Core of Perylenetetracarboxylic Bisimides," Eur. J. Org. Chem. 2000(2):365-380.
Li et al. (2006) "Poly(2,7-Carbazole) and Perylene Tetracarboxydiimide: A Promising Donor/acceptor Pair for Polymer Solar Cells," J. Mater. Chem. 16:96-100.
Li et al. (Oct. 2014) "Achieving Balanced Intermixed and Pure Crystalline Phases in PDI-Based Non-Fullerene Organic Solar Cells via Selective Solvent Additives," Phys. Chem. Chem. Phys. 16:26917-26928.
Lin et al. (Mar. 2014) "A Star-Shaped Perylene Diimide Electron Acceptor for High-Performance Organic Solar Cells," Adv. Mater. 26:5137-5142.

(56) References Cited

OTHER PUBLICATIONS

Lin et al. (May 2014) "A Twisted Dimeric Perylene Diimide Electron Acceptor for Efficient Organic Solar Cells," Adv. Energy Mater. 4:1400420.

Liu et al. (Feb. 2014) "A Multifunctional Perylenediimide Derivative (DTPDI) Can Be Used as a Recyclable Specific Hg2+ Ion Sensor and an Efficient DNA Delivery Carrier," J. Mater. Chem. B. 2:2093-2096.

Liu et al. (Sep. 2015) "Pyrene Terminal Functionalized Perylene Diimide as Non-Fullerene Acceptors for Bulk Heterojunction Solar Cells," RSC Adv. 5:83155-83163.

Lüttich et al. (2012) "Interface Properties of OFETs Based on an Air-Stable N-Channel Perylene Tetracarboxylic Diimide Semiconductor," Phys. Status Solidi A. 209:585-593.

McAfee et al. (Apr. 2016) "The Optimization of Direct Heteroarylation and Sonogashira Cross-Coupling Reactions as Efficient and Sustainable Synthetic Methods to Access π-Conjugated Materials with Near-Infrared Absorption," ACS Sustainable Chem. Eng. 4:3504-3517.

McAfee et al. (Feb. 2015) "Utility of a Heterogeneous Palladium Catalyst for theSynthesis of a Molecular Semiconductor via Stille, Suzuki, and Direct Heteroarylation Cross-Coupling Reactions," RSC Adv. 5:26097-26106.

McAfee et al. (Jan. 2017) "Simply Complex: The Efficient Synthesis of an Intricate Molecular Acceptor for High-Performance Air-Processed and Air-Tested Fullerene-Free Organic Solar Cells," Chem. Mater. 29:1309-1314.

Mei et al. (Aug. 2015) "Side Chain Engineering in Solution-Processable Conjugated Polymers," Chem. Mater. 26:604-615.

Meng et al. (Published Online Dec. 13, 2015) "High-Performance Solution-Processed Non-Fullerene Organic Solar Cells Based on Selenophene-Containing Perylene Bisimide Acceptor," J. Am. Chem. Soc. 138:375-380.

Qian et al. (2009) "Heterocyclic Annelated Di(perylene Bisimide): Constructing Bowl-Shaped Perylene Bisimides by the Combination of Steric Congestion and Ring Strain," J. Org. Chem. 74:6275-6282.

Qiu et al. (2005) "Facile Synthesis of Carbazole-Containing Semiladder Polyphenylenes for Pure-Blue Electroluminescence," Macromolecules. 38(16):6782-6788.

Rajasingh et al. (2007) "Selective Bromination of Perylene Diimides under Mild Conditions," J. Org. Chem. 72:5973-5979.

Sun et al. (Aug. 2015) "Non-Fullerene Acceptor-Based Bulk Heterojunction Organic Solar Cells with Efficiency over 7%," J. Am. Chem. Soc. 137:11156-11162.

Sun et al. (May 2016) "Perylene Diimide Based All Small-Molecule Organic Solar Cells: Impact of Branched-Alkyl Side Chains on Solubility, Photophysics, Self-Assembly, and Photovoltaic Parameters," Org. Electron. 35:151-157.

Tilley et al. (Apr. 2015) "Thionation Enhances the Electron Mobility of Perylene Diimide for High Performance N-Channel Organic Field Effect Transistors," Adv. Funct. Mater. 25:3321-3329.

Yan et al. (Aug. 2013) "Towards Rational Design of Organic Electron Acceptors for Photovoltaics: A Study Based on Perylenediimide Derivatives," Chem. Sci. 4:4389-4394.

Zang et al. (Jun. 2014) "Integrated Molecular, Interfacial, and Device Engineering towards High-Performance Non-Fullerene Based Organic Solar Cells," Adv. Mater. 26:5708-5714.

Zhan et al. (2007) "A High-Mobility Electron-Transport Polymer with Broad Absorption and Its Use in Field-Effect Transistors and All-Polymer Solar Cells," J. Am. Chem. Soc. 129:7246-7247.

Zhan et al. (2011) "Rylene and Related Diimides for Organic Electronics," Adv. Mater. 23:268-284.

Zhang et al. (Nov. 2015) "A Selenophenyl Bridged Perylene Diimide Dimer as an Efficient Solution-Processable Small Molecule Acceptor," Chem. Commun. 51:1058-1061.

Zhong et al. (Oct. 2014) "Efficient Organic Solar Cells with Helical Perylene Diimide Electron Acceptors," J. Am. Chem. Soc. 136:15215-15221.

Vespa, M. et al. (Jul. 2018) "Synthesis of a Perylene Diamide Dimer with Pyrrolic N—H Bonds and N-Functionalized Derivatives for Organic Field-Effect Transistors and Organic Solar Cells," Eur. J. Org. Chem. 4592-4599.

Wang, H. et al. (Sep. 2017) "A simple molecular structure of ortho-derived perylene diimide diploid for non-fullerene organic solar cells with efficiency over 8%," J. Mater. Chem. A. 5:22288-22296.

Wang, H. et al. (Aug. 2017) "Heterologous perylene diimide arrays: potential non-fullerene acceptors in organic solar cells," J. Mater. Chem. C, 5:8875-8882.

* cited by examiner

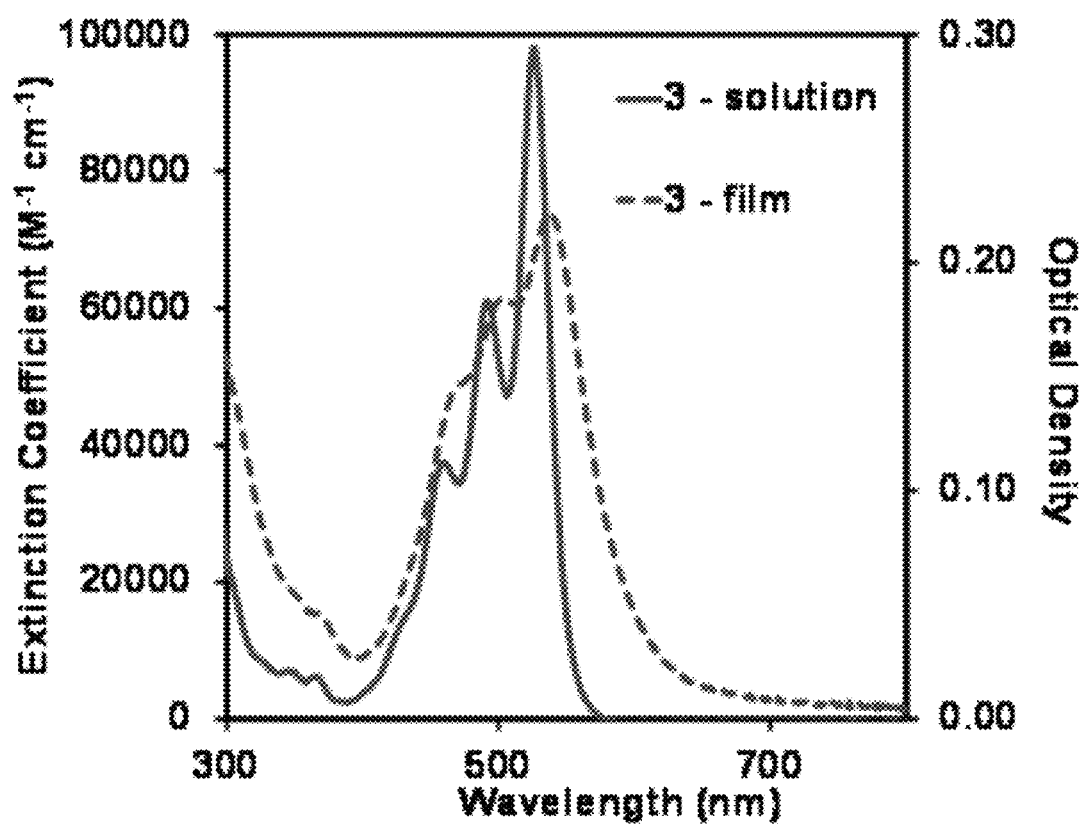
FIG: 3

N-ANNULATED PERYLENE DIIMIDE DIMERS WITH ACTIVE PYRROLIC N—H BONDS

BACKGROUND

Perylene diimide (PDI) based compounds represent an important class of opto-electronically active materials that are useful in a wide variety of applications, including application as active components in organic solar cells (OSC) [2-4], fluorescent probes in imaging studies [5-7], chemical sensors [8-11], and semiconducting material in organic field effect transistors (OFETs). [12-14] PDI based materials can be synthesized from relatively inexpensive starting materials, and have appreciable and tunable visible light absorption, strong self-assembly characteristics, and low-lying frontier molecular orbitals, that make them useful as electron transport materials in optoelectronic devices. [15-19]

OSC's can provide low-cost, clean energy with minimal environmental impact. [20-22] Fullerenes have been employed as the electron transport material within the active layer of the highest performing OSC devices. [23-27] Soluble PDI based materials are considered as attractive alternatives to fullerenes. [17, 28-33] Functionalized PDI materials exhibit a low lying lowest unoccupied molecular orbital (LUMO) which facilities electron transfer reactions, making them good electron acceptors. Importantly, functionalized PDI derivatives have several advantages over fullerenes, including: low cost, synthetic modularity and increased light absorption in the visible region.

PDI molecules have been functionalized at the imide position with alkyl groups and at the bay position with aromatic units or certain heteroatoms to improve solubility and tailor self-assembly (Formula A) [3,19,34-37]:

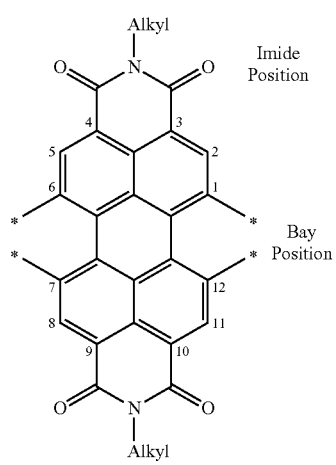

For example, dimerization of the PDI chromophore and incorporation of the heteroatoms S or Se in the bay positions of the PDI framework [3,36,37] provided a material having a remarkable effect on both its inter- and intramolecular properties, allowing the fabrication of OSCs with power conversion efficiencies (PCEs) up to 7.1% and 8.4% for the S and Se annulated derivatives, respectively, when paired with tailor-made donor-acceptor type π-conjugated polymers [3,31,32]:

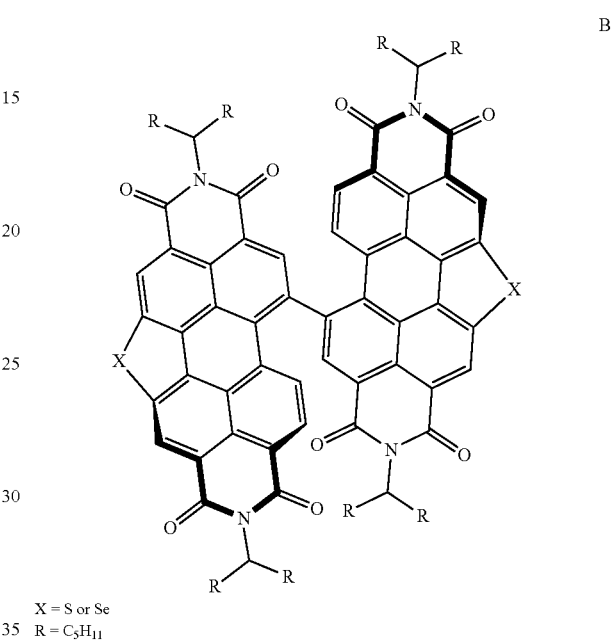

Further derivatization of the dimers of Formula B is limited and large branched alkyl chains are required to ensure adequate organic solvent solubility.

Preferred PDI materials for use as an electron acceptor in OSCs will exhibit high solubility in organic solvents to allow for a diverse array of solution processing protocols to be employed, can be prepared by high yielding and scalable synthetic methods using atom-economical and sustainable chemistry practice, employ modular synthesis allowing for preparation of a library of diverse functionalized materials and maintain the key optical and electronic properties of related PDIs, including strong visible light absorption and deep LUMO energy levels.

Langhalls et al. [39] reported the synthesis of certain PDI materials having a heterocyclic pyrrolic unit installed at the bay position of the chromophore. While these materials were synthesized in good yields, they were not explored as electronically active materials to be self-assembled into superstructures useful for charge transport.

Published US patent application 2017/0352812 published Dec. 7, 2017 relates to certain PDI derivatives of formula:

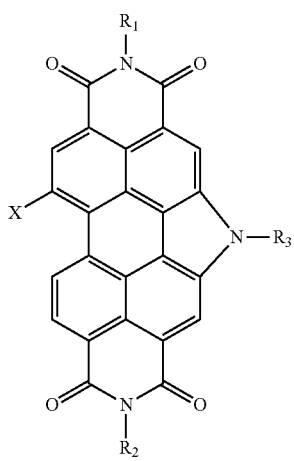

where X is a halogen, triflyl, tosyl or mesyl group, $R_1$ and $R_2$ are straight-chain or branched alkyl groups and R3 is a straight-chain or branched alkyl group. The application also related to PDI dimers of formula:

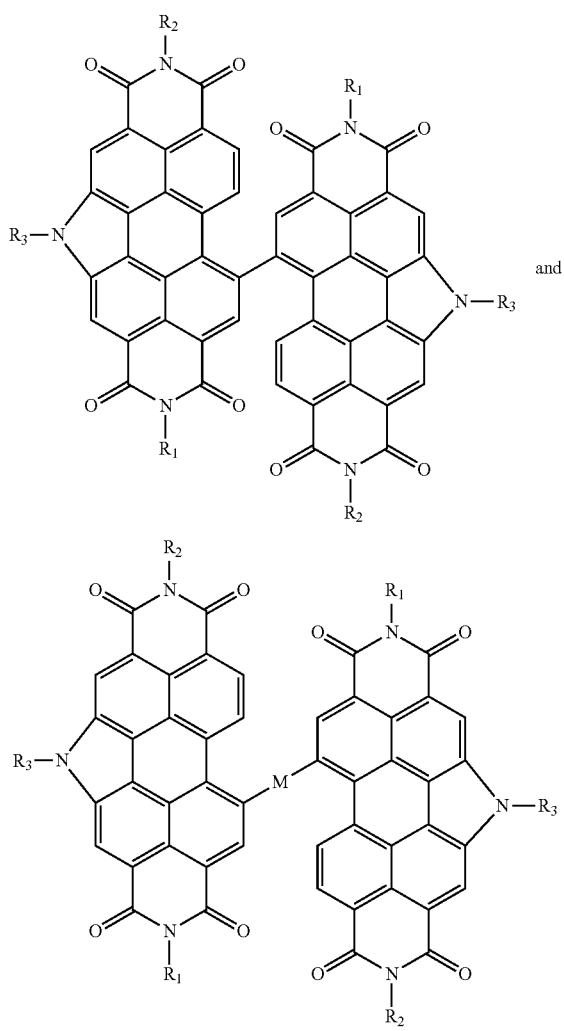

and where $R_1$-$R_3$ are as defined for the monomer and M is certain divalent linking moieties. The reference also related to certain PDI containing polymers of formula:

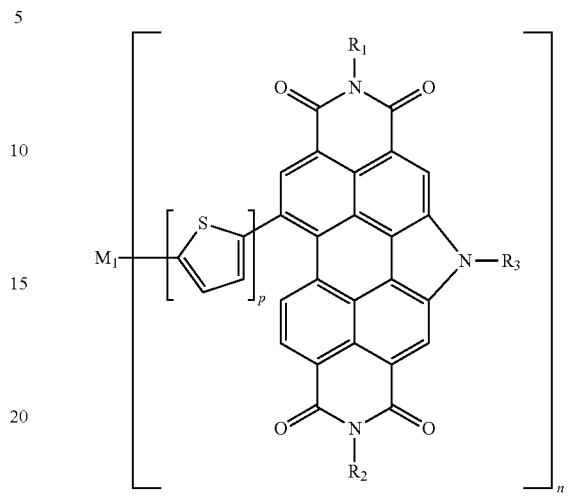

where $R_1$-$R_3$ are as defined for the monomer, p is 1 or 0, n is 2, 3 or 4 and $M_1$ is certain divalent, trivalent or tetravalent moieties.

The present invention relates to PDI dimers with active pyrrolic N—H bonds and polymers of such PDIs useful as starting materials for the preparation of additional derivatized PDI dimers and polymers as well as useful as electronically active materials. Derivatized PDI dimers herein could not be readily synthesized by prior art methods.

SUMMARY

The invention relates to certain PDI derivatives useful as opto-electronically active materials or for the synthesis of such materials. Certain compounds herein function as efficient electron acceptors and are useful as electron active components of electronic devices.

The invention provides compounds of Formula I:

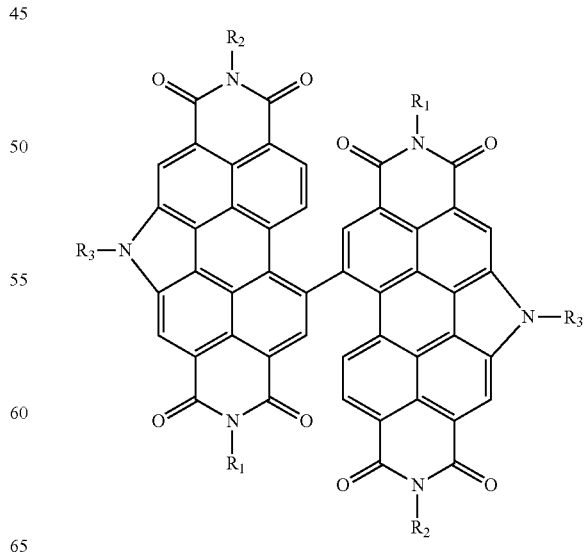

and salts thereof, where:

$R_1$- and $R_2$ are the same or different and are independently selected from straight-chain and branched alkyl groups having 1-30 carbon atoms; and (1) both $R_3$ are hydrogen (compounds of Formula IA, see below);

(2) each $R_3$ may be the same group or different groups and both are independently selected from amine protecting groups (compounds of formula IB, see below);

(3) each $R_3$ may be the same group or different groups and each $R_3$ is independently selected from halogenated straight-chain alkyl groups having 1 to 30 carbon atoms or halogenated branched alkyl groups having 3-30 carbon atoms, one or more alkoxyalkyl groups linked through an at least divalent linker to the pyrrole nitrogen, an optionally substituted aryl, an optionally substituted arylalkyl, an optionally substituted heterocyclyl and an optionally substituted heteroaryl group. (compounds of Formula IC and Formula ID, see below).

In specific embodiments of Formula I and each of Formulas IA-ID, $R_1$ and $R_2$ are independently selected from a straight-chain alkyl having 10 or more carbon atoms or a branched chain alkyl having 3 to 20 carbon atoms.

In specific embodiments of Formula I and each of Formulas IA-ID, $R_1$ and $R_2$ are independently selected from a straight-chain alky having 3 to 9 carbon atoms. In specific embodiments, $R_1$ and $R_2$ are independently selected from a branched-chain alky having 3 to 10 carbon atoms. In specific embodiments, $R_1$ and $R_2$ are the same group. In specific embodiments, $R_1$ and $R_2$ are selected from branched alkyl groups of formula —C(Ra)(Rb), where Ra and Rb are, independently, alkyl groups having 2-10 carbon atoms. In specific embodiments, Ra and Rb are the same alkyl group. In specific embodiments, Ra and Rb are different alkyl groups. In specific embodiments, Ra and Rb are straight-chain alkyl groups.

In specific embodiments of Formula I and each of Formulas IA-ID, $R_1$ and $R_2$ are independently a 1-ethylpropyl, 1-propylbutyl, 1-butylpentyl, 1-pentylhexyl, 1-hexylheptyl, 1-heptyloctyl, 1-octylnonyl, 1-nonyldecyl, or 2-ethylhexyl.

In specific embodiments of Formula I and each of Formulas IA-ID, $R_1$ and $R_2$ are the same alkyl group. In specific embodiments, $R_1$ and $R_2$ are different alkyl groups. In specific embodiments, $R_1$ and $R_2$ are both 1-ethylproypl groups.

In specific embodiments of Formula I and each of Formulas IA-ID, $R_1$ and $R_2$ are independently selected from branched alkyl groups having 3-8 carbon atoms. In specific embodiments, $R_1$ and $R_2$ are the same branched alkyl groups.

In specific embodiments of Formula I and each of Formulas IA-ID, $R_1$ and $R_2$ are unsubstituted alkyl groups.

In specific embodiments of Formula I, optionally substitution of aryl, arylalkyl, heterocyclic and heteroaryl groups is substitution with one or more halogen, hydroxyl, nitro, cyano, alkyl, alkoxy, alkoxyalkyl, haloalkyl, unsubstituted phenyl, unsubstituted benzyl, optionally substituted phenyl, optionally substituted benzyl, amino, alkylamino, dialkyl amino, —$N^+(R_d)_3$, Oxo, —COX (where X is a halogen), —CO—$R_d$, —$CO_2$—$R_d$, —CO—$N(R_d)_2$, —$OCOR_d$, —$NHCOR_d$, —$SO_3R_d$, or —$SR_d$, where $R_d$ is hydrogen or C1-C8 alkyl. Where a substituent is or contains an alkyl group, the alkyl group can be a C1-C3 alkyl group and more specifically, a methyl, ethyl or propyl group.

In specific embodiments, optional substitution of an aryl group includes substitution with 1, 2, 3, 4, or 5 halogens. Specific halogens are fluorine, chlorine or bromine. In specific embodiments, optional substitution of an aryl group includes substitution with an amino or dimethylamino group. In specific embodiments, optional substitution of an aryl group includes substitution with a methyl group or a methoxy group. In specific embodiments, optional substitution of an aryl group includes substitution with 1, 2 or 3 hydroxy groups. In specific embodiments, optional substitution of an aryl group includes substitution with an alkoxyalkyl group.

In an embodiment, compounds of Formula IA are employed as starting materials for the preparation of compounds of Formula IB, IC and ID.

In specific embodiments, compounds of Formula IA can be prepared by deprotection of the amine groups of corresponding compounds of Formula IB.

In specific embodiments, compounds of Formula IB are employed to prepare solid forms, such as films, layers, or coatings of the corresponding compounds of Formula IA. Compounds of Formula IA are generally less soluble in organic solvents than corresponding compounds of Formula IB. Organic solvents useful in processing of materials include halogenated solvents such as chloroform, methylene chloride and chlorobenzene, but also more environmentally friendly non-halogenated solvents such as xylene (e.g., o-xylene) and trimethylbenzene. The solvent 2-methyl tetrahydrofuran is also of potential use in such processing. Solutions of compounds of Formula IB in such organic solvents can be employed to prepare solid forms, such as films, layers or coatings of Compounds of Formula IB, by casting from such solutions with evaporation of organic solvent. Such solid forms of compounds of Formula IB can be chemically reacted or heated to remove amine protecting groups providing solid forms of corresponding compounds of Formula IA.

More specifically, a film of a compound of Formula IA, where both $R_3$ are hydrogen is prepared from a cast film of a compound of Formula IB, where both $R_3$ are amine protecting groups. The film of the compound of Formula IB is prepared for example by casting a film from a solution of the compound of Formula IB in an organic solvent. The prepared film of the compound of Formula IB is then treated to remove the amine protecting groups converting the film to a film of the corresponding compound of Formula IA. The protecting groups can be removed by heating the film to a temperature of at least about 170° C. More specifically, the protecting groups can be removed by heating the film to a temperature between about 170° C. to 225° C. Heating being continued until the protecting groups are removed. Yet more specifically, the film is treated at a temperature of 200° C. for 10-30 minutes. Yet more specifically, the film is treated at a temperature of 200° C. for 10 minutes. The organic solvent can be selected, for example, from chloroform or methylene chloride. In a specific embodiment, the compound of Formula IB is a compound in which $R_3$ is —CO—PR, where PR is an alkyl group and more specifically is a t-butyl group.

Compounds of Formula IA can also be employed to prepare copolymers with various dihaloaryl compounds via Ullman type reactions. Such copolymers include statistical copolymers and random copolymers. Such copolymers include those of Formulas III and IIIA.

The invention provides an electronic device employing an electron acceptor wherein the electron acceptor is one or more compounds of Formula I.

The invention provides an organic solar cell employing an electron acceptor wherein the electron acceptor is one or more compounds of Formula I.

The invention provides an organic thin film transistor employing an electron acceptor wherein the electron acceptor is one or more compounds of Formula I.

The invention provides a redox flow battery which comprises one or more compounds of Formula I.

Other embodiments of the invention will be apparent on review of the detailed description, the examples and the drawings.

BRIEF DESCRIPTION OF THE DRAWINGS

FIG. 3 is the UV-visible spectrum of compound 3 measured in CHCl$_3$ solution and as a cast film.

FIGS. 5A, 5B and 50C are DSC plots for compounds 3, 4 and 5, respectively.

DETAILED DESCRIPTION

Figure 1:
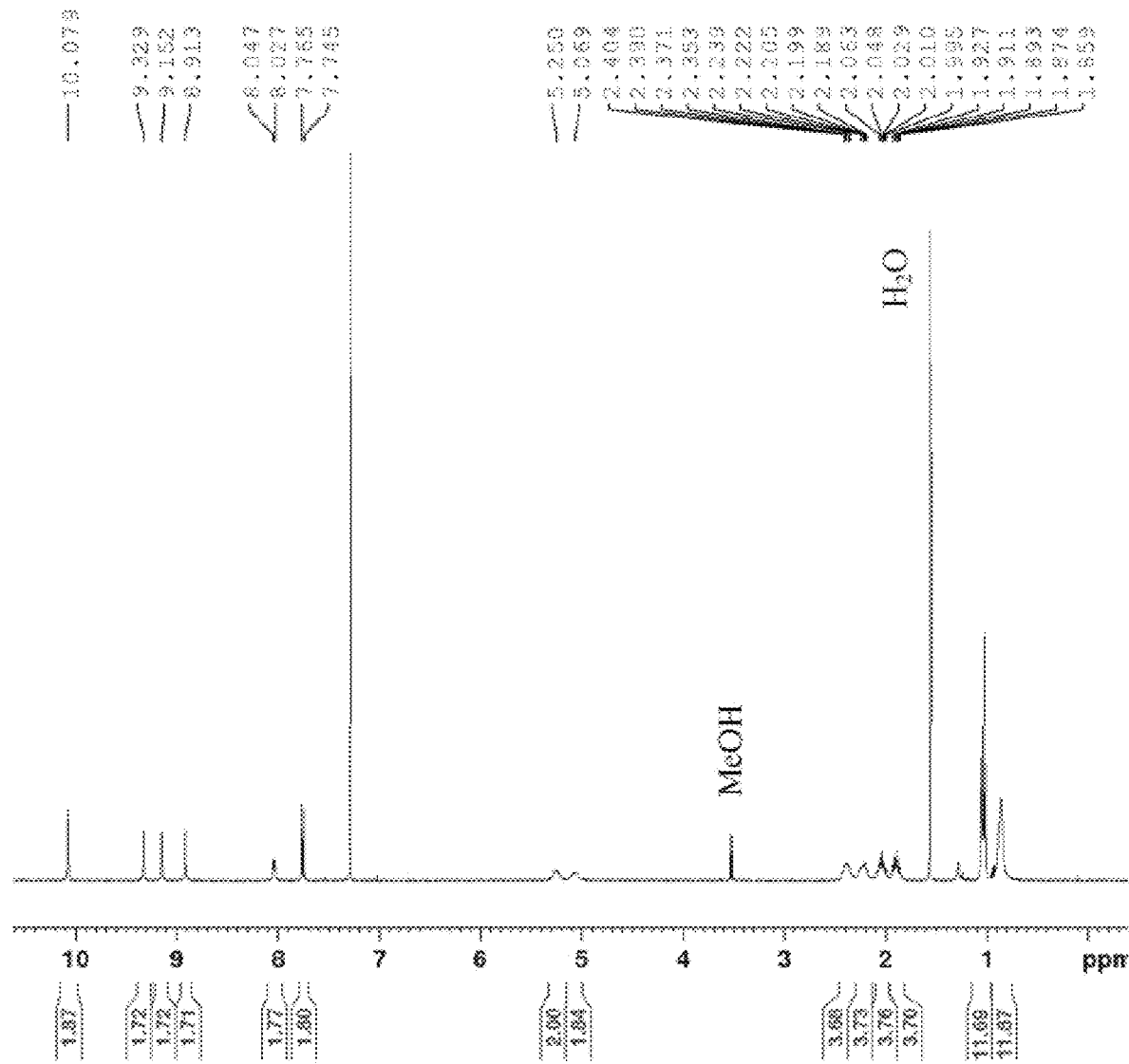
FIG. 1 provides the $^1$HNMR spectrum of compound 3 run in CDCl$_3$.

The invention provides PDI dimers of Formula I:

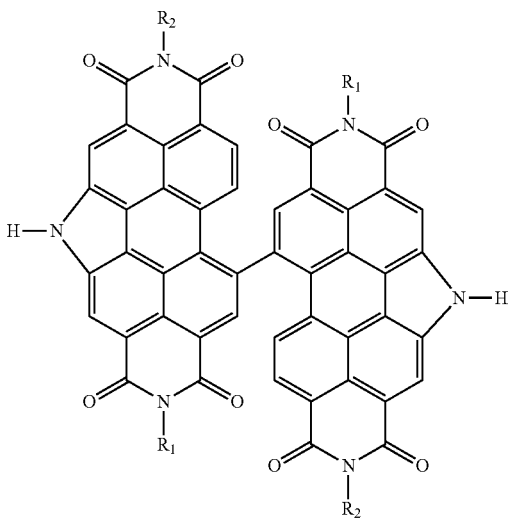

and salts thereof,
where:
$R_1$- and $R_2$ are the same or different and are independently selected from straight-chain and branched alkyl groups having 1-30 carbon atoms; and
(1) both $R_3$ are hydrogen (compounds of formula IA see below);
(2) each $R_3$ may be the same group or different groups and both are independently selected from amine protecting groups (compounds of formula IB see below);
(3) each $R_3$ may be the same group or different groups and each $R_3$ is independently selected from halogenated straight-chain alkyl groups having 1 to 30 carbon atoms or halogenated branched alkyl groups having 3-30 carbon atoms, one or more alkoxyalkyl groups linked through an at least divalent linker to the pyrrole nitrogen, an optionally substituted aryl, an optionally substituted arylalkyl, an optionally substituted heterocyclyl and an optionally substituted heteroaryl group. (compounds of Formula IC and Formula ID, see below).

In specific embodiments of Formula I and each of Formulas IA-ID, $R_1$ and $R_2$ are independently selected from a straight-chain alkyl having 10 or more carbon atoms or a branched chain alkyl having 3 to 20 carbon atoms.

In specific embodiments of Formula I and each of Formulas IA-ID, $R_1$ and $R_2$ are independently selected from a straight-chain alky having 3 to 9 carbon atoms. In specific embodiments, $R_1$ and $R_2$ are independently selected from a branched-chain alky having 3 to 10 carbon atoms. In specific embodiments, $R_1$ and $R_2$ are the same group. In specific embodiments, $R_1$ and $R_2$ are selected from branched alkyl groups of formula —C(Ra)(Rb), where Ra and Rb are, independently, alkyl groups having 2-10 carbon atoms. In specific embodiments, Ra and Rb are the same alkyl group. In specific embodiments, Ra and Rb are different alkyl groups. In specific embodiments, Ra and Rb are straight-chain alkyl groups.

In specific embodiments of Formula I and each of Formulas IA-ID, $R_1$ and $R_2$ are independently a 1-ethylpropyl, 1-propylbutyl, 1-butylpentyl, 1-pentylhexyl, 1-hexylheptyl, 1-heptyloctyl, 1-octylnonyl, 1-nonyldecyl, or 2-ethylhexyl.

In specific embodiments of Formula I and each of Formulas IA-ID, $R_1$ and $R_2$ are the same alkyl group. In specific embodiments, $R_1$ and $R_2$ are different alkyl groups. In specific embodiments, $R_1$ and $R_2$ are both 1-ethylproypl groups.

In specific embodiments of Formula I and each of Formulas IA-ID, $R_1$ and $R_2$ are independently selected from branched alkyl groups having 3-8 carbon atoms. In specific embodiments, $R_1$ and $R_2$ are the same branched alkyl groups.

In specific embodiments of Formula I and each of Formulas IA-ID, $R_1$ and $R_2$ are unsubstituted alkyl groups.

In specific embodiments of Formula I, optionally substitution of aryl, arylalkyl, heterocyclic and heteroaryl groups is substitution with one or more halogen, hydroxyl, nitro, cyano, alkyl, alkoxy, alkoxyalkyl, haloalkyl, unsubstituted phenyl, unsubstituted benzyl, optionally substituted phenyl, optionally substituted benzyl, amino, alkylamino, dialkyl amino, —N$^+$(R$_d$)$_3$, Oxo, —COX (where X is a halogen), —CO—R$_d$, —CO$_2$—R$_d$, —CO—N(R$_d$)$_2$, —OCOR$_d$, —NHCOR$_d$, —SO$_3$R$_d$, or —SR$_d$, where R$_d$ is hydrogen or C1-C8 alkyl. Where a substituent is or contains an alkyl group, the alkyl group can be a C1-C3 alkyl group and more specifically, a methyl, ethyl or propyl group.

In specific embodiments, optional substitution of an aryl group includes substitution with 1, 2, 3, 4, or 5 halogens. Specific halogens are fluorine, chlorine or bromine. In specific embodiments, optional substitution of an aryl group includes substitution with an amino or dimethylamino group. In specific embodiments, optional substitution of an aryl group includes substitution with a methyl group or a methoxy group. In specific embodiments, optional substitution of an aryl group includes substitution with 1, 2 or 3 hydroxy groups. In specific embodiments, optional substitution of an aryl group includes substitution with an alkoxyalkyl group.

The invention provides compounds of Formula IA:

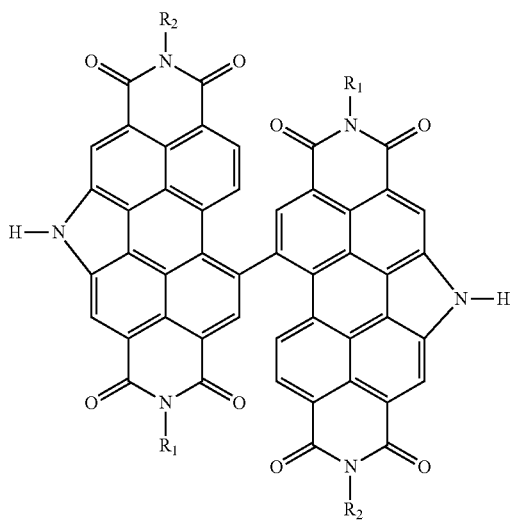

and salts thereof, wherein $R_1$ and $R_2$ are as defined for Formula I.

Compounds of Formula IA are useful as electronic materials and also are useful as a starting material for preparation of electronic materials as described herein, including compounds of Formulas IC and ID, as well as polymers as described herein.

The invention provides compounds of Formula IB:

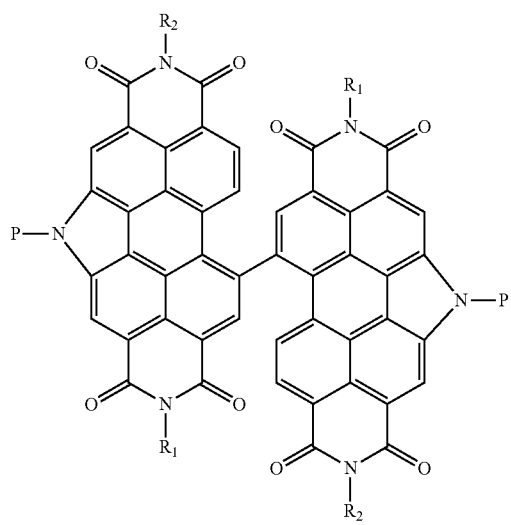

and salts thereof,
wherein:

P is an amine protecting group and in particular is an amine protecting group. In a specific embodiment, the P group is removable on heating the compound to a temperature ranging from about 170° C. to about 225° C. In a specific embodiment, the P group is removable by chemical treatment of the compound with acid, such as trifluoroacetic acid or hydrobromic acid The compounds of Formula IB are useful for preparation of certain PDI derivatives and also for the preparation of films and other solid forms of corresponding compounds of Formula IA. Such solid forms can be prepared for example by casting onto inert substrates, such as those made from glass, quartz, metal, or plastic. In specific embodiments, the substrate is inert to chemical treatment or heating to remove the protecting group.

Compounds of Formula IB are generally more soluble in organic solvents than the corresponding compounds of Formula IA and can be more readily formed into solid films, coating, or layers by casting onto or molding on substrates from organic solutions. Once formed into a desired film, coating, or layer, the solid form is chemically treated to remove P or heated to between about 170° C. to 225° C. to remove P. This process facilitates formation of a solid form of the compounds of Formula IA.

In a specific embodiment of Formula IB, P is a —CO—PR group which is an amine protecting group) and PR is an —OR' group where R' is a straight-chain or branched chain unsubstituted alkyl, an optionally substituted aryl group, an optionally substituted arylakyl group, a halogenated alkyl group having 1 to 12 carbon atoms, or an optionally substituted sulfonylaryl group (—SO$_2$-Aryl).

In a more specific embodiment of Formula IB, PR is a t-butyl group (BOC), a fluorenylmethyl (FMOC) group, an optionally-substituted benzyl group (CBz), a trifluoromethyl group, pentafluoroethyl group, a trichloroethyl group (Troc), a sulfonylaryl group (—SO$_2$-Aryl), e.g., a tosyl, nosylate, p-fluoro-phenyl-SO$_2$—, or a pentafluoro-SO$_2$.

Compounds of Formula IA and IB are useful as a starting material for the synthesis of electronic materials as described herein and are also useful as electronic materials.

The invention also provides compounds of Formula IC:

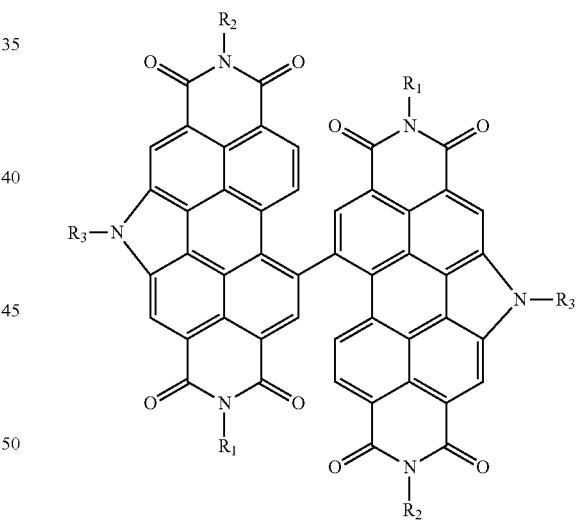

and salts thereof wherein $R_1$ and $R_2$ are as defined for Formula I and each $R_3$ may be the same or different and each $R_3$ is independently selected from:
  halogenated straight-chain alkyl groups having 1 to 30 carbon atoms or halogenated branched alkyl groups having 3-30 carbon atoms, and
  one or more alkoxyalkyl groups linked through an at least divalent linker to the pyrrole nitrogen.

In specific embodiments, $R_3$ is a fluorinated alkyl group having 1-12 carbon atoms or a fluorinated alkyl group having 1-8 carbon atoms, or a fluorinated alkyl group having 1-6 carbon atoms. In specific embodiments, $R_3$ is a perfluorinated alkyl group having 1-12 carbon atoms or a perfluorinated alkyl group having 1-8 carbon atoms, or a perfluorinated alkyl group having 1-6 carbon atoms. In these preceding embodiments, the fluorinated or perfluorinated alkyl group can be straight-chain or branched alkyls. More specifically, $R_3$ is perfluoromethyl, perfluoroethyl, perfluoro-n-propyl, perfluoro-n-butyl, perfluoro-n-pentyl, perfluoro-n-hexane, perfluoro-n-heptyl, perfluoro-n-octyl, perfluoro-n-nonyl, perfluoro-n-decyl, perfluoro-n-undecyl, or perfluoro-n-dodecyl. In specific embodiments, both $R_3$ are the same fluorinated or perfluorinated alkyl group.

In a specific embodiment, $R_3$ is a partially fluorinated alkyl group of formula:

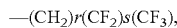
—(CH$_2$)$_r$(CF$_2$)$_s$(CF$_3$), where r and s are integers and r is 1-10 and s is 1-10 and r+s is 2-20 or 2-12 or 6-20 or 6-12.

$R_3$ groups which are fluorinated or perfluorinated alkyl groups can be prepared by reaction of a compound of Formula IA with, for example, a monobrominated fluoroalkane or a monobrominated perfluoroalkane. Starting halogenated alkanes for the preparation of compounds of Formula IC from compounds of Formula IA are commercially available or can be prepared by art recognized methods.

In specific embodiments, $R_3$ is an alkoxyalky group linked to the PDI dimer via an amide, ester or carbonate moiety. In specific embodiments, $R_3$ is a group of formula:

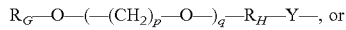
R$_G$—O—(—(CH$_2$)$_p$—O—)$_q$—R$_H$—Y—, or

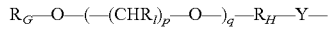
R$_G$—O—(—(CHR$_I$)$_p$—O—)$_q$—R$_H$—Y— where:

p is an integer 2-4, q is an integer 1-30, $R_G$ is a C1-C4 alkyl, $R_H$ is a C1-C4 alkylene, $R_I$ is independently a hydrogen or a C1-C3 alkyl and Y is —CO—, —O—CO—, or —NH—CO—. In more specific embodiments, $R_G$ is methyl or ethyl, $R_I$ is methyl or ethyl; $R_H$ is —CH$_2$—CH$_2$—, —CH$_2$—CH(CH$_3$)— or —CH(CH$_3$)—CH$_2$—, p is 2, q is 1-10 and Y is —CO—, —O—CO—, or —NH—CO—. In more specific embodiments, $R_G$ is methyl or ethyl, $R_I$ is methyl or ethyl; $R_H$ is —CH$_2$—CH$_2$—, —CH$_2$—CH(CH$_3$)— or —CH(CH$_3$)—CH$_2$—, p is 2, q is 1-10 and Y is —CO—. In more specific embodiments, $R_3$ is $R_G$—O—(CH$_2$—CH$_2$—O)$_q$—CH$_2$—CH$_2$—CO—, where $R_G$ is methyl or ethyl, and q is an integer from 1-30, or an integer from 1-20, or an integer from 1-12, or an integer from 1-10, or an integer from 1-8. In specific embodiments, both $R_3$ are the same group.

$R_3$ groups containing alkoxyalkyl groups can be prepared, for example, by reaction of compounds of Formula IA with known pegylation reagents which react with secondary amine groups. Specific pegylation reagents useful for such preparation are those carrying a reactive ester group, such as an NHS ester.

The invention also provides compounds of Formula ID:

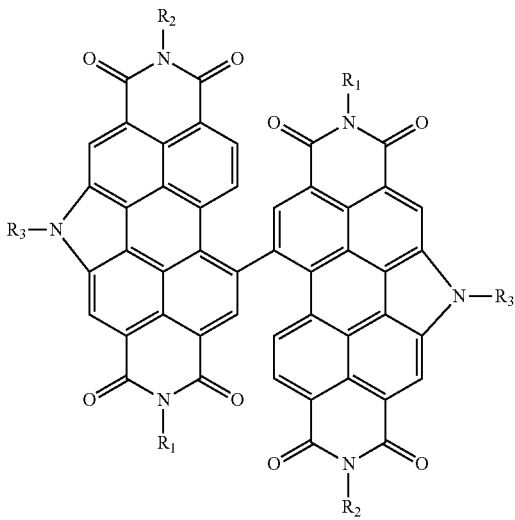

and salts thereof wherein $R_1$ and $R_2$ are as defined for Formula I and each $R_3$ may be the same or different and each $R_3$ is independently selected from:

an optionally substituted aryl, an optionally substituted arylalkyl, an optionally substituted heterocycyl and an optionally substituted heteroaryl group.

In specific embodiments of Formula ID, $R_3$ is an optionally substituted phenyl or an optionally substituted benzyl group. In specific embodiments, $R_3$ is a para-substituted phenyl, where the para-substituent is an amino group, an alkyl amino group, a dialkyl amino group or an alkoxy group. In specific embodiments, $R_3$ is a para-substituted phenyl, where the para-substituent is a cyano, a nitro or a —SO$_2$R$_K$ group, where $R_K$ is hydrogen, a C1-C6 alkyl or a phenyl group. In specific embodiments, $R_3$ is p-cyanotetrafluorophenyl, or pentafluorophenyl.

In specific embodiments, $R_3$ is a 5- or 6-member ring heterocylic group which has one or two heteroatoms (N, O or S) in the ring and is saturated or unsaturated. More specifically, $R_3$ is a heteroaryl group of formula:

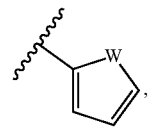

where W is S, O or NH.

In specific embodiments of Formulas IB, IC and ID both $R_3$ groups are the same group.

In specific embodiments of Formula ID, both $R_3$ are optionally substituted phenyl or benzyl groups. In specific embodiments, optionally substitution of phenyl or benzyl groups includes substitution of the aryl ring with 1-5 halogens, particularly 1-5 fluorines. In specific embodiments, optionally substitution of phenyl or benzyl groups includes substitution of the aryl ring with 1-5 electron withdrawing groups. In specific embodiments, optionally substitution of phenyl or benzyl groups includes substitution of the aryl ring with 1-5 electron donating groups. Electron withdrawing groups include among others trifluoromethyl, trichloromethyl, cyano, sulfonate ammonium, tri or tetra alkyl ammonium, formyl (—COH), acyl (—COR$_e$, where Re is alkyl), —COOR$_d$, —CONH$_2$ or halide. Electron donating groups include among others, amino groups, alkyl amino groups, dialkyl amino groups, alkyl, hydroxyl, alkoxy, —OCOR$_d$, phenyl and vinyl groups (—CR$_d$═C(R$_d$)$_2$).

Compounds of Formula ID can be prepared by reaction of compounds of Formula I by methods that are known in the art, for example, Buchwald-Hartwig cross coupling reactions can be employed to introduce aryl, heterocyclic or heteroaryl groups at positions R$_3$ in compounds of Formula IA.

In other embodiments, the invention provides co-polymers of Formulas III or IIIA:

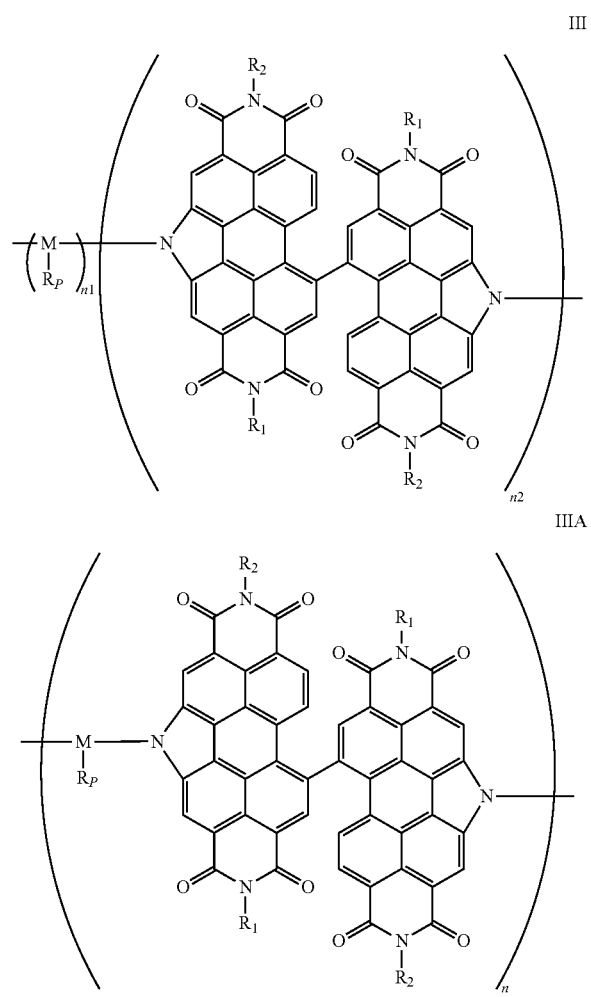

where R$_1$ and R$_2$ are as defined in Formula I, M is an optionally substituted alkylene or is an optionally substituted arylene group (AR), and R$_P$ represents non-hydrogen substituents on the indicated M group or mores specifically on the AR group, n1, n2 and n are the number of the indicated repeating units. In specific embodiments, the alkylene group has 1-20 carbon atoms, or 2-20 carbon atoms, or 2-12 carbon atoms, or 6-20 carbon atoms or 6-12 carbon atoms. In specific embodiments, R$_P$ represents no substitution. In specific embodiments, R$_P$ represents substitution on the alkylene with 1-40 substituents, e.g., a perhalogenated alkylene. More specifically, R$_P$ represents substitution on the alkylene of 1-10, 1-6 or 1-3 substituents. In specific embodiments, the arylene group AR is unsubstituted. In other embodiments, the AR is substituted with 1-12 substituents.

Formula III generally represents a co-polymer of the indicated polymer components. Co-polymers of Formula III include statistical copolymer, including random co-polymers, as well as various block copolymers. Formula IIIA represents an alternating copolymer of the indicated polymer components. In specific embodiments, n1+n2 range from 1-about 100, 2 to about 100, 10 to about 100, 2 to 10, 2 to 20, 2 to 50, or 10 to 50. In specific embodiments, n1 is greater than n2. In other embodiments, n2 is greater than n1. In specific embodiments, n1 ranges from 2 to about 98 and n2 ranges from 2 to about 98. In specific embodiments, n is 2-100, or 2-50, or 2-20, or 2-10, or 10-100, or 10-50, or 10-20.

In specific embodiments, AR is an optionally substituted divalent phenylene, optionally substituted divalent biphenylene, or an optionally substituted divalent naphthylene. More specifically, AR is an optionally substituted 1,4-phenylene, an optionally substituted 1,3-phenylene, an optionally substituted 1,4'-biphenylene, an optionally substituted 2,6-naphthylene, an optionally substituted 2,7-naphthylene, or an optionally substituted 1,5-naphthylene. Optional substitution includes substitution with one or more substituents selected from halogen, alkyl, alkoxy, alkoxyalkyl, cyano, nitro, or hydroxyl.

Copolymers of Formulas III and IIIA can be prepared from compounds of Formula IA by methods that are well known in the art and, for example, by reaction of a dimer of Formula IA with a dibromoaryl compound, such as 1,4-dibromobenzene under Ullman Reaction conditions or with a dibromoalkyl compound, such as 1,6-dibromohexane or 1,8-dibromooctane.

In an embodiment the invention provides a polyimide polymer, such as those of Formula III or IIIA, which is prepared by copolymerization of a compound of Formula IA with a dibromoaryl or a dibromoalkyl compound.

Definitions

The term alkyl refers to a monovalent group formally derived from a saturated hydrocarbon group by removal of a hydrogen. An alkyl group has the general formula C$_n$H$_{2n+1}$. Alkyl groups can be straight-chain (linear) or branched. Alkyl groups herein can have 1-30 carbon atoms and more preferably 1-20 carbon atoms. Branched alkyl groups herein have 3-30 carbon atoms and more preferably 3-20 carbon atoms. Straight-chain alkyl groups include those having 1-3 carbon atoms, 1-6 carbon atoms, 4-8 carbon atoms, 6-10 carbon atoms, and 6-20 carbon atoms, among other groups of carbon atom range. Straight-chain alkyl groups include methyl, ethyl, propyl, hexyl, heptyl, octyl, nonyl, decyl, dodecyl individually or in any combination. Branched alkyl groups include isopropyl, iso-butyl, sec-butyl, 1-ethylpropyl, 1-propylbutyl, 1-butylpentyl, 1-pentylhexyl, 1 hexylheptyl, 1-heptyloctyl, 1-octylnonyl, 1 nonyldecyl, 2-ethylhexyl individually or in any combination. Branching may occur anywhere along the alkyl chain from the site of attachment of the alkyl group. For example, a branch may occur at the first carbon (as in al-ethylpropyl group). The branching can occur for example at the second carbon along the chain (e.g., 2-ethylhexyl). There may be multiple branches along the chain (e.g., 1-ethyl-5-methylhexyl). In specific embodiments, a branched alkyl chain has one branching point which is at the first, second or third carbon from the site of attachment.

An alkoxy group is an alkyl group, as broadly discussed above, linked to oxygen ($R_{alkyl}$—O—).

A divalent alkyl group is called an alkylene group herein. Such a group is attached between to other moieties by formation of a bond to two carbons in the group. The alkylene group is one example of a divalent linker. The term alkylene refers to a divalent radical of a straight-chain or branched saturated hydrocarbon. Alkylene groups can have 1-12 carbon atoms unless otherwise indicated. Alkylene groups include those having 2-12, 2-8, 2-6 or 2-4 carbon atoms. Linker groups ($L_1$) herein include alkylene groups, particularly straight chain, unsubstituted alkylene groups, —$(CH_2)_n$—, where n is 1-12, n is 1-10, n is 1-9, n is 1-8, n is 1-7, n is 1-6, n is 1-5, n is 1-4, n is 1-3, n is 2-10, n is 2-9, n is 2-8, n is 2-7, n is 2-6, n is 2-5 or n is 2-4.

An alkoxyalkyl group is an alkyl group in which one or more of the non-adjacent internal —$CH_2$— groups are replaced with —O—, such a group may also be termed an ether group. These groups may be straight-chain or branched, but straight-chain groups are preferred. Alkoxyalkyl groups include those having 2-12 carbon atoms and 1, 2, 3 or 4 oxygen atoms. More specifically, alkoxyalkyl groups include those having 3 or 4 carbons and 1 oxygen, or those having 4, 5 or 6 carbons and 2 oxygens. Each oxygen in the group is bonded to a carbon in the group. The group is bonded into a molecule via a bond to a carbon in the group.

An alkoxyalkylene group is a divalent alkoxyalkyl group. This group can be described as an alkylene group in which one or more of the internal —$CH_2$— groups are replaced with an oxygen. These groups may be straight-chain or branched, but straight-chain groups are preferred. Alkoxyalkylene groups include those having 2-12 carbon atoms and 1, 2, 3 or 4 oxygen atoms. More specifically, alkoxyalkylene groups include those having 3 or 4 carbons and 1 oxygen, or those having 4, 5 or 6 carbons and 2 oxygens. Each oxygen in the group is bonded to a carbon in the group. The group is bonded into a molecule via bonds to a carbon in the group. Linker groups ($L_1$) herein include alkoxyalkylene groups, particularly straight chain, unsubstituted alkoxyalkylene groups. Specific alkoxyalkylene groups include, among others, —$CH_2$—O—$CH_2$—, —$CH_2$—$CH_2$—O—$CH_2$—$CH_2$—, —$CH_2$—$CH_2$—$CH_2$—O—$CH_2$—$CH_2$—$CH_2$—, —$CH_2$—$CH_2$—O—$CH_2$—, —$CH_2$—O—$CH_2$—$CH_2$—, —$CH_2$—$CH_2$—O—$CH_2$—$CH_2$—O—$CH_2$—, —$CH_2$—$CH_2$—O—$CH_2$—$CH_2$—O—$CH_2$—$CH_2$—, —$CH_2$—$CH_2$—O—$CH_2$—$CH_2$—$CH_2$—O—$CH_2$—, —$CH_2$—$CH_2$—$CH_2$—O—$CH_2$—$CH_2$—$CH_2$—O—$CH_2$—$CH_2$—.

In some embodiments herein an alkoxyalkyl group is bonded indirectly via a linking moiety to a pyrrole nitrogen. This linking moiety is the residue of reaction that bonds the alkoxyalkyl group to the nitrogen. The linking moiety can, for example, be —CO— (a carbonyl), where an amide bond (—CO—N<) is formed with the nitrogen. The linking group, can, for example, be —O—CO— (a carboxyl), where a carbamate bond (—O—CO—N<) is formed with the nitrogen. The linking group can, for example, be —NH—CO— (an amide), where a ureylene (urea, —NH—CO—N<) moiety is formed. Methods for attaching alkoxyalkyl groups to amines are known in the art.

The term acyl group refers to the group —CO—R where R is hydrogen, an alkyl or aryl group as described herein. The group —CO— $CH_3$ is an acetyl group.

The term amino group refers to the species —$N(H)_2$. The term alkylamino refers to the species —NHR" where R" is an alkyl group, particularly an alkyl group having 1-3 carbon atoms. The term dialkylamino refers to the species —$NR"_2$ where each R" is independently an alkyl group, particularly an alkyl group having 1-3 carbon atoms. Dialkyl amino groups also include those in which the two R" groups together with the N to which they are bonded form a heterocyclic or heteroaryl ring. Such amino heterocyclic or heteroaryl groups are bonded to other moieites through the nitrogen atom.

Aryl groups include groups having one or more 5- or 6-member aromatic rings. Aryl groups can contain one, two or three, 6-member aromatic rings. Aryl groups can contain two or more fused aromatic rings. Aryl groups can contain two or three fused aromatic rings. Aryl groups are optionally substituted with one or more non-hydrogen substituents. Substituted aryl groups include among others those which are substituted with alkyl or alkenyl groups, which groups in turn can be optionally substituted. Specific aryl groups include phenyl groups, biphenyl groups, and naphthyl groups, all of which are unsubstituted or optionally substituted as described herein. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated (perfluorinated) or partially fluorinated aryl groups, such as aryl groups having one or more hydrogens replaced with one or more fluorine atoms.

Arylalkyl groups are those in which an alkyl group is substituted with an aryl group. Arylalkyl groups include benzyl and phenethyl groups among others. Most generally alkyl groups are straight-chain or branched as described herein. In specific embodiments, the alkyl groups of arylalkyl groups have 1-6 carbon atoms and more preferably 1-3 carbon atoms. Arylalkyl groups can contain any aryl group as described herein. Arylalkyl groups are optionally substituted as described herein. Substituted arylalkyl groups include those in which the aryl group is substituted with 1-5 non-hydrogen substituents and particularly those substituted with 1, 2 or 3 non-hydrogen substituents. Useful substituents include among others, methyl, methoxy, hydroxy, halogen, and nitro. Particularly useful substituents are one or more halogens. Specific substituents include F, Cl, and nitro.

A divalent arylene (AR) moiety is derived from an aromatic hydrocarbon formally by removal of two hydrogens. Arylene groups herein include those derived from an aromatic hydrocarbon have one or more aromatic hydrocarbon rings which include those with fused rings. More specifically, the arylene group can include 1, 2, 3 or 4 aromatic rings. In specific embodiments, arylene groups are optionally substituted with one or more alkyl groups, halogens or CN groups. Arylene groups include among others phenylene, biphenylene, and naphthylene.

Divalent moieties include arylene groups having available two sites of attachment:

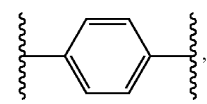

phenyl(1,4)ene

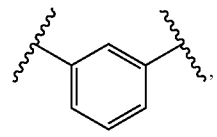

phenyl(1,3)ene

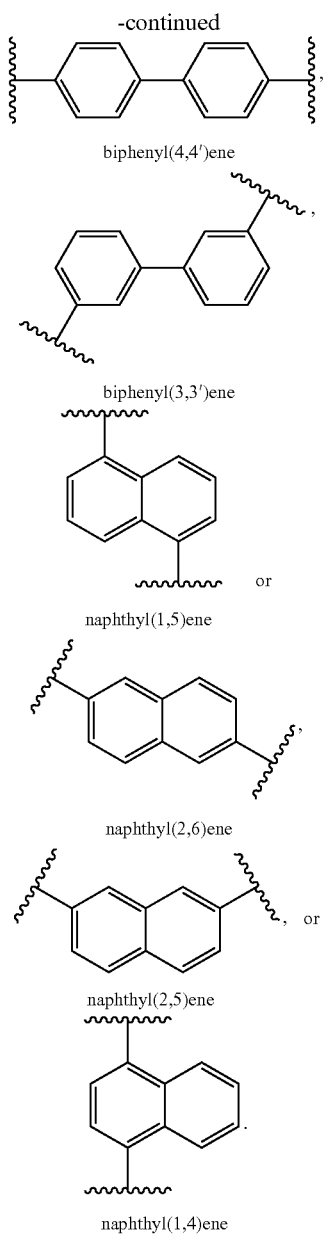

biphenyl(4,4')ene biphenyl(3,3')ene naphthyl(1,5)ene or naphthyl(2,6)ene naphthyl(2,5)ene, or naphthyl(1,4)ene.

A heterocyclic (heterocyclyl) group is a group having one or more saturated or unsaturated carbon rings and which contains one to three heteroatoms (e.g., N, O or S) per ring. These groups optionally contain one, two or three double bonds. To satisfy valence requirement, a ring atom may be substituted as described herein. One or more carbons in the heterocyclic ring can be —CO— groups. Heterocyclic groups include those having 3-12 carbon atoms, and 1-6, heteroatoms, wherein 1 or 2 carbon atoms are replaced with a —CO— group. Heterocyclic groups include those having 3-12 or 3-10 ring atoms of which up to three can be heteroatoms other than carbon. Heterocyclic groups can contain one or more rings each of which is saturated or unsaturated. Heterocyclic groups include bicyclic and tricyclic groups. Preferred heterocyclic groups have 5- or 6-member rings. Heterocyclic groups are optionally substituted as described herein. Specifically, heterocyclic groups can be substituted with one or more alkyl groups. Heterocyclic groups include those having 5- and 6-member rings with one or two nitrogens and one or two double bonds. Heterocyclic groups include those having 5- and 6-member rings with an oxygen or a sulfur and one or two double bonds. Heterocyclic groups include those having 5- or 6-member rings and two different heteroatoms, e.g., N and O, O and S or N and S. Specific heterocyclic groups include among others, pyrrolidinyl, piperidyl, piperazinyl, pyrrolyl, pyrrolinyl, furyl, thienyl, morpholinyl, oxazolyl, oxazolinyl, oxazolidinyl, indolyl, triazoly, and triazinyl groups.

Heteroaryl groups include groups having one or more aromatic rings in which at least one ring contains a heteroatom (a non-carbon ring atom). Heteroaryl groups include those having one or two heteroaromatic rings carrying 1, 2 or 3 heteroatoms and optionally have one 6-member aromatic ring. Heteroaryl groups can contain 5-20, 5-12 or 5-10 ring atoms. Rings of the group may be fused. Heteroaryl groups include those having one aromatic ring contains a heteroatom and one aromatic ring containing carbon ring atoms. Heteroaryl groups include those having one or more 5- or 6-member aromatic heteroaromatic rings and one or more 6-member carbon aromatic rings. Heteroaromatic rings can include one or more N, O, or S atoms in the ring. Heteroaromatic rings can include those with one, two or three N, those with one or two O, and those with one or two S, or combinations of one or two or three N, O or S. Specific heteroaryl groups include furyl, pyrrolyl, pyridinyl, pyrazinyl, pyrimidinyl, quinolinyl, purinyl, thiophenyl, or indolyl groups.

Heteroatoms include O, N, S, P or B. More specifically heteroatoms are N, O or S. In specific embodiments, one or more heteroatoms are substituted for carbons in aromatic or carbocyclic rings. To satisfy valence any heteroatoms in such aromatic or carbocyclic rings may be bonded to H or a substituent group, e.g., an alkyl group or other substituent.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

With respect to the various compounds of the disclosure, the atoms therein may have various isotopic forms (e.g., isotopes of hydrogen include deuterium and tritium). All isotopic variants of compounds of the disclosure are included within the disclosure and particularly include deuterium and $^{13}C$ isotopic variants. It will be appreciated that such isotopic variants may be useful for carrying out various chemical and biological analyses, investigations of reaction mechanisms and the like. Methods for making isotopic variants are known in the art.

Compounds of the disclosure can be prepared by one of ordinary skill in the art in view of the descriptions provided herein and what is known in the art from commercially or otherwise readily available starting materials and reagents. As described herein in the Examples, known synthetic methods can be readily adapted for synthesis of the compounds of the formulas herein.

Compounds of the disclosure may contain chemical groups (acidic or basic groups) that can be in the form of salts. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (e.g., organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the present disclosure, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the disclosure. Additionally, inventive compounds may have trans and cis isomers and may contain one or more chiral centers, therefore exist in enantiomeric and diastereomeric forms. The disclosure includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form. The term enantiomerically pure refers to a sample containing molecules of a given structure whose molecules have the same chirality sense (i.e., are the same optical isomer) within the limits of detection. The term substantially enantiomerically pure refers to a sample containing molecules of a given structure, wherein equal to or less than 1% of the molecules of the sample have a different chirality sense. Compounds of the invention include those which are enatiomerically pure and those that are substantially enatiomerically pure.

With respect to the various compounds of the disclosure, the atoms therein may have various isotopic forms (e.g., isotopes of hydrogen include deuterium and tritium). All isotopic variants of compounds of the disclosure are included within the disclosure and particularly include deuterium and $^{13}C$ isotopic variants. It will be appreciated that such isotopic variants may be useful for carrying out various chemical and biological analyses, investigations of reaction mechanisms and the like. Methods for making isotopic variants are known in the art.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore exist in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

With respect to the various compounds of the invention, the atoms therein may have various isotopic forms, e.g., isotopes of hydrogen include deuterium and tritium. All isotopic variants of compounds of the invention are included within the invention and particularly included at deuterium and $^{13}C$ isotopic variants. It will be appreciated that such isotopic variants may be useful for carrying out various chemical and biological analyses, investigations of reaction mechanisms and the like. Methods for making isotopic variants are known in the art.

In specific embodiments, synthetic reactions are carried out as described in the Examples herein with the proviso that starting materials for reactions are chosen to obtain the desired alkyl substituents at $R_1$, $R_2$ and $R_3$.

One of ordinary skill in the art will recognize that starting materials and reagents other than those specifically disclosed in the Examples can be employed in the reactions herein without resort to undue experimentation. One of ordinary skill in the art knows how to select appropriate starting materials for alkylation and to if necessary adjust the solvent employed.

In embodiments, the disclosure provides an electronic device employing an electron acceptor wherein the electron acceptor is one or more compounds of formulas herein.

In embodiments, the disclosure provides an organic solar cell which comprises one or more compounds of any one of the formulas herein which is an electron acceptor.

In embodiments, the disclosure provides an organic thin film transistor which comprises one or more compounds of any one of the formulas herein which is an electron acceptor.

In embodiments, the disclosure provides a redox flow battery which comprises one or more compounds of any one of the formulas herein which is an electron acceptor.

Those of ordinary skill in the art will appreciate that methods for the preparation of organic solar cells, organic thin film transistors and redox flow batteries are known in the art and can be applied employing materials of the formulas herein. In view of what is known in the art and what is described herein one of ordinary skill in the art can employ materials described and characterized herein in such devices without resort to undue experimentation.

Additional details of the synthesis, characterization and application of PDI materials are provided in references 38, 39, 43, 43, 53, 57, 64, 66, 67, 70, 71, 78-81 and any supporting information of each of these references which is freely available on-line for the publisher. Additional details of processing of materials, such as PDI materials of the invention, and the preparation of devices, such as organic solar cells are provided in references 41, 44, 46, 51, 52, 54, 55, 56, 58, 59, 60, 61-63, 66, -68, 70-76 and 79-81 and any supporting information of each of these references which is freely available on-line for the publisher. Each of these references and any corresponding supporting information is incorporated by reference herein in its entirety for such additional details including synthetic methods, purification methods, characterization of compounds, processing of PDT materials, components of devices employing these materials and methods for such characterization, construction and testing of organic solar cell, as well as structure and components of organic solar cells.

US patent publication 20170352812 is incorporated by reference herein in its entirety for additional methods of synthesis of starting materials useful in the synthesis of compounds of this invention and for additional description of application of the materials of this invention. A. Hendsbee, (June 2017) Conjugated Organic Molecules Containing Imide Functional Groups for Organic Electronics, PhD Thesis University of Calgary, Calgary, Alberta CA, Chapter 7 pages 106-130 and Chapter 8 pages 131-190 are each incorporated by reference herein in its entirety for methods of synthesis and processing of materials applicable to the materials herein.

All references throughout this application, for example patent documents including issued or granted patents or equivalents; patent application publications; and non-patent literature documents or other source material; are hereby incorporated by reference herein in their entireties, as though individually incorporated by reference. All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

Example 1: Synthesis

Scheme 1 illustrates the synthesis of compound 3, the perylene diimide dimer, tPDI2N—H, with active pyrrolic N—H bonds.

Scheme 1: Synthesis of compounds 2-6 using a multi-pathway approach.
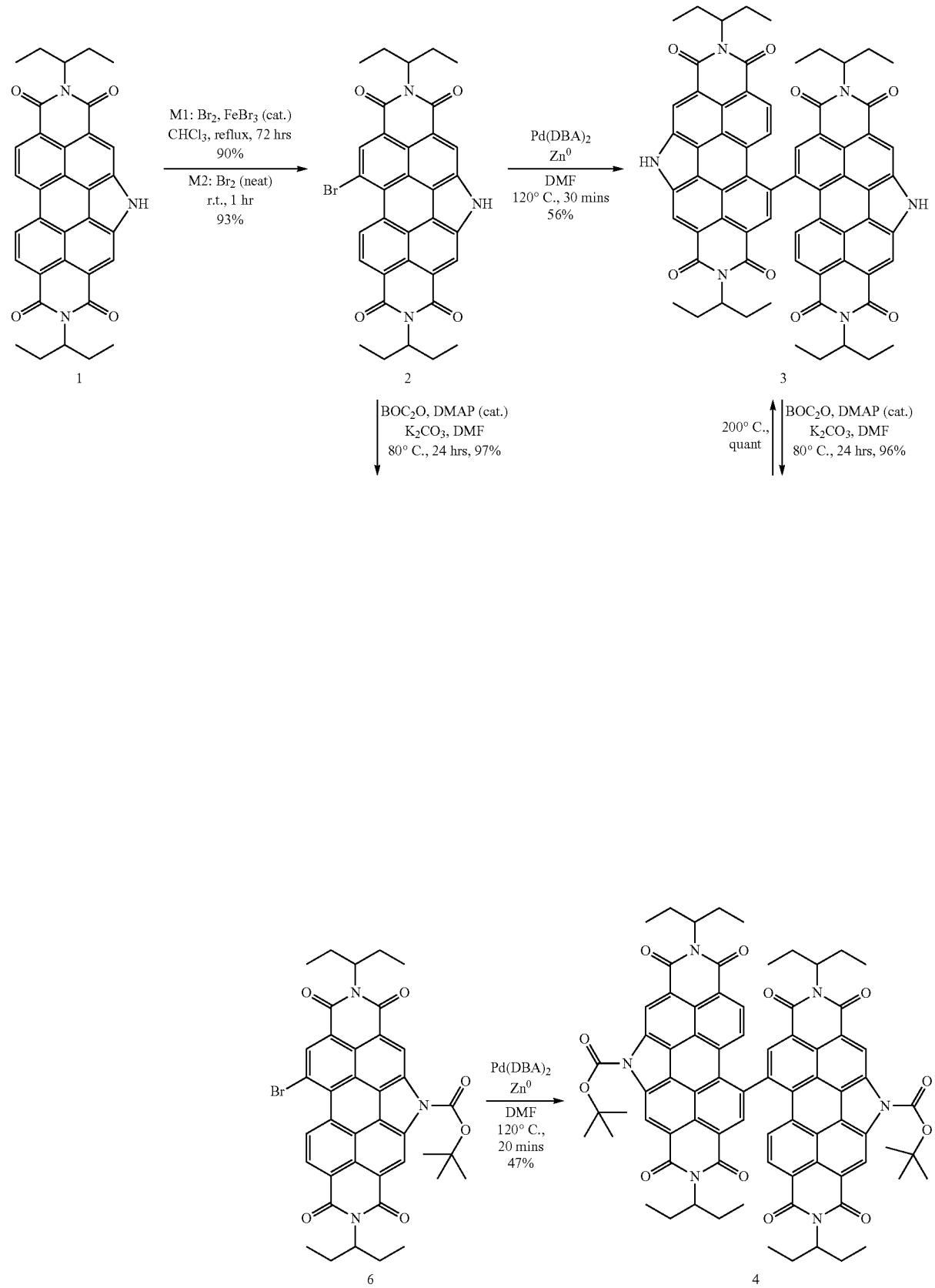

-continued

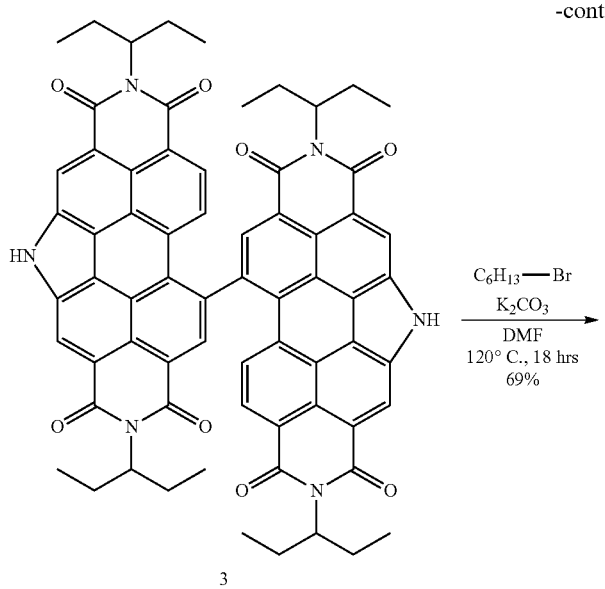
3

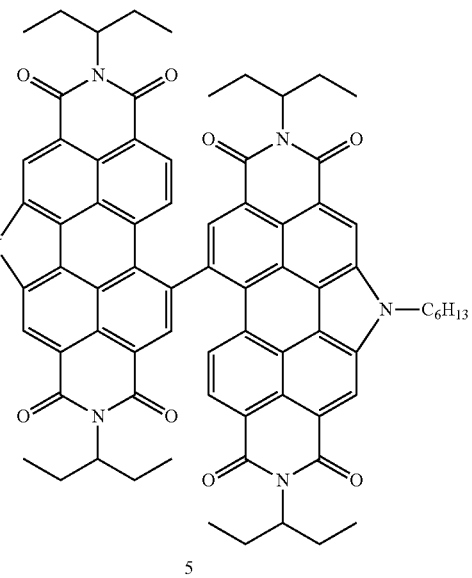
5

Compound 3 is prepared directly from the bromine monomer 2 or from the amine protected dimer 4. Compound 3 is employed, for example, as a starting material for C derivatives substituted at the pyrrolic NH as illustrated by alkylation of compound 3 to form compound 5.

1.1: Synthesis of BrPDIN-H (2)

-continued

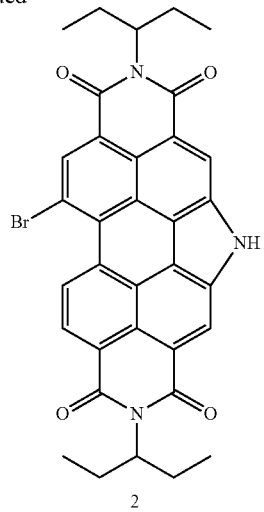
2

Synthesis of BrPDIN-H (2)

Method 1:

PDIN-H (1) (1.74 g, 3.20 mmol, 1.00 eq.) and iron powder (0.106 g, 1.90 mmol, 0.59 eq.) were added to a 1 L flask and dissolved in chloroform (500 mL). While stirring, excess bromine (~9 mL, 0.175 mol, XS eq.) was added by Pasteur pipette, a vented condenser was affixed to the flask and the solution was heated to reflux. After reacting for 72 hours, TLC indicated complete consumption of the starting material. Air was bubbled through the mixture for 3 hours to remove excess bromine and the solution was concentrated under reduced pressure using a rotary evaporator. The resulting residue was taken up in methanol (200 mL) and vacuum filtered to yield a red, opaque solid (1.75 g, 90%). MS (APCI): expected 623.13, found 623.14.

Method 2:

PDIN-H (1) (200 mg, 0.368 mmol, 1.00 eq.) was placed in a 25-mL microwave vial equipped with a magnetic stir bar

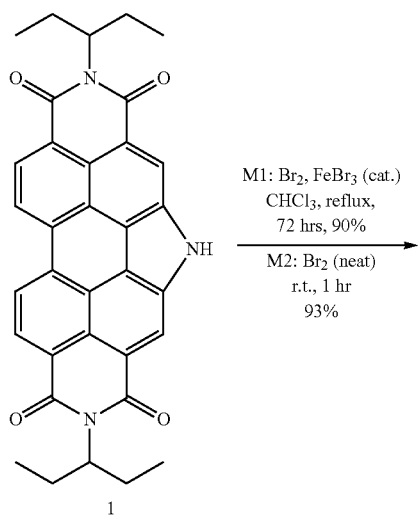
1 and a Pasteur pipette full of liquid bromine (~1.5 mL, 4.6 g, 29.3 mmol.) was added. The vial was capped and the slurry was stirred vigorously at room temperature for one hour until TLC indicated complete consumption of the starting material. To remove excess bromine, air was bubbled through the suspension until no brown marks were observed on a piece of paper towel that was held at the mouth of the vial. The residue was taken up in dichloromethane (50 mL) and concentrated under reduced pressure using a rotary evaporator. The resulting solid was slurried in methanol (50 mL) and vacuum filtered to yield a red, opaque solid (212 mg, 93%).

1.2: Synthesis of tPDI$_2$N—H (3) (Method 1)

Synthesis of tPDI$_2$N—H Dimer (3)

Method 1:

BrPDIN-H (100 mg, 0.16 mmol, 1.00 eq.), bis(dibenzylideneacetone)palladium(0) (20 mg, 0.035 mmol, 20 mol %) and zinc dust (51 mg, 0.78 mmol, 4.88 eq.) were added to a 20-mL microwave vial equipped with a magnetic stir bar. The vial was capped, the head space was purged with N$_2$ gas for 10 minutes and dry DMF was added via cannula transfer. The solution was heated to 120° C. while stirring. After 15 minutes, the solution went from deep red to purple. After 30 minutes, TLC indicated complete consumption of the starting material (2). The vial was cooled to room temperature, the cap was removed and the solution was poured into dichloromethane (100 mL). The solution was passed through a 1-inch silica plug and then concentrated under reduced pressure on a rotary evaporator. The resulting solid was slurried in water (25 mL) and vacuum filtered to yield a dark red solid. This was purified using a silica column and a 20% acetone in dichloromethane gradient, resulting in a red, opaque solid (98 mg, 56%). $^1$H NMR (Chloroform-d, TMS/ppm) δ: 10.08 (s, 2H), 9.33 (s, 2H), 9.16 (s, 2H), 8.91 (s, 2H), 8.03 (d, 2H), 7.75 (d, 2H), 5.25 (m, 2H), 5.06 (m, 2H), 2.37 (m, 4H), 2.20 (m, 4H), 2.03 (m, 4H), 1.97 (m, 4H), 1.03 (t, 12H), 0.85 (bs, 12H). $^{13}$C NMR (ppm): 140.3, 133.5, 133.2, 132.7, 130.1, 126.4, 124.5, 124.3, 123.1, 122.2, 120.3, 120.0, 57.5, 57.2, 29.1, 24.5, 11.0, 10.7. MS (ESI): expected 1085.42, found 1085.42.

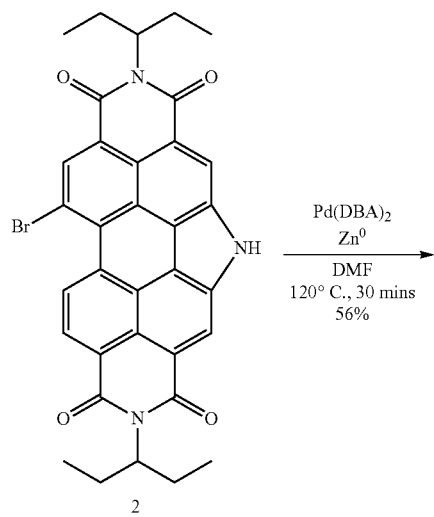

1.3 Synthesis of tPDI$_2$N—BOC (4) (Method 1)

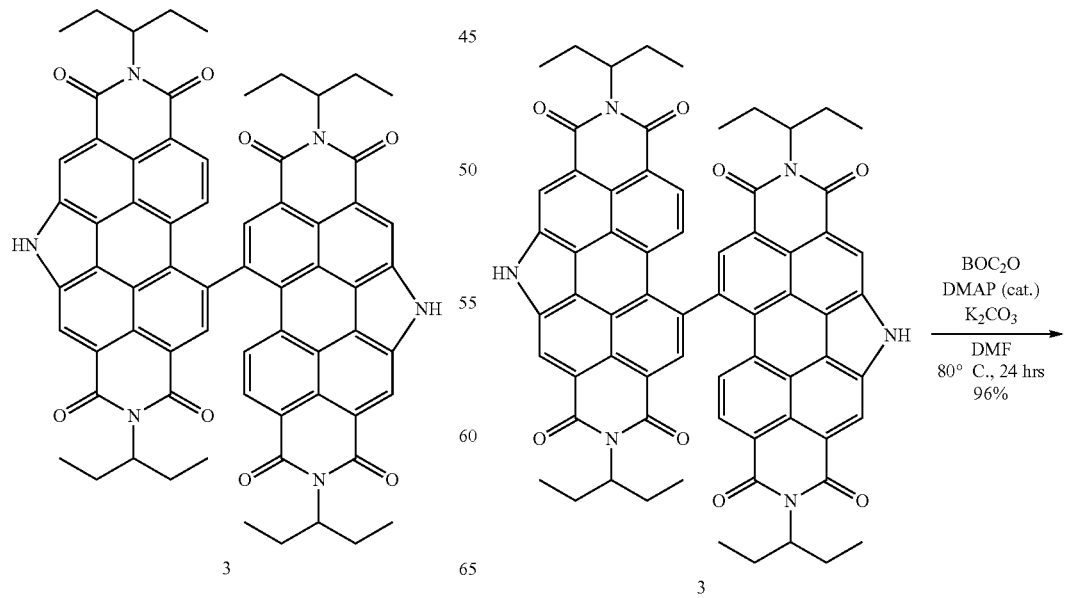

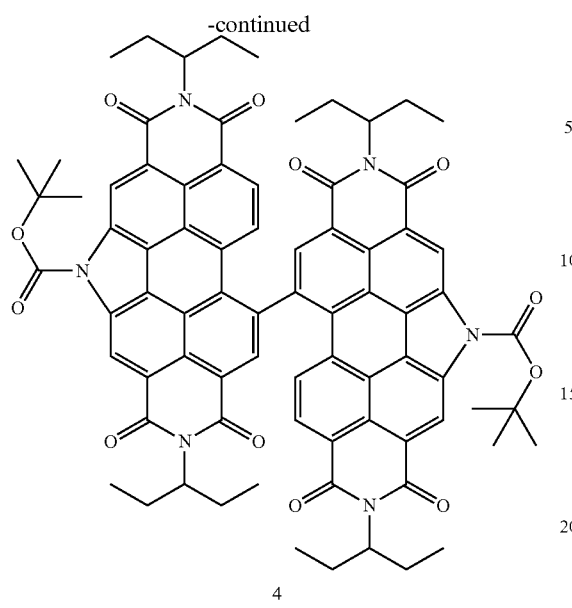

Synthesis of tPDI₂N—BOC Dimer (4)

Method 1:

tPDI₂N—H (3) (350 mg, 0.323 mmol, 1.00 eq.) and 4-dimethyaminopyridine (6 mg, 0.052 mmol, 0.16 eq.) were placed in a 25-mL bomb flask equipped with a magnetic stir bar. The vessel was capped and the headspace was purged with N₂ gas for 5 minutes. Anhydrous DMF (15 mL) was added via cannula transfer and the vessel was purged with N₂ gas for an additional 5 minutes. The flask was heated to 80° C., di-tert-butyl-carbonate (0.16 mL, 155 mg, 0.711 mmol, 2.20 eq.) was added by syringe and the solution was stirred for 2 hours. The bomb cap was then removed, potassium carbonate (50 mg, 0.350 mmol, 1.10 eq.) was quickly added and a new cap was placed on the bomb. The solution was stirred for an additional 22 hours at 80° C. After TLC had indicated complete consumption of the starting material, the solution was concentrated under reduced pressure using a rotary evaporator. The residue was taken up in dichloromethane (100 mL), placed in a separatory funnel and extracted using a distilled water wash (1×50 mL) followed by a brine wash (1×50 mL). The organic phase was then collected, dried over MgSO₄ and filtered through a silica plug. The solution was concentrated under reduced pressure using a rotary evaporator and the resulting solid was slurried in methanol (75 mL). The solution was subsequently vacuum filtered to yield the title product as a fine, red powder (400 mg, 96%). $^1$H NMR (Chloroform-d, TMS/ppm) δ: 9.66 (s, 2H), 9.47 (s, 2H), 8.81 (s, 2H), 8.04 (d, 2H), 7.71 (d, 2H), 5.19 (m, 2H), 5.03 (m, 2H), 2.34 (m, 4H), 2.18 (m, 4H), 2.01 (m, 4H), 1.99 (bs, 12H), 1.86 (m, 4H), 0.99 (t, 9H), 0.82 (bm, 9H). $^{13}$C NMR (ppm): 149.1, 131.7, 124.6, 122.8, 119.8, 86.4, 57.4, 35.9, 30.9, 27.7, 24.6, 11.1. MS (APCI): expected 1286.53, found 1286.52.

1.4: Synthesis of tPDI₂N—H (3) from tPDI₂N—BOC (4) (Method 2)

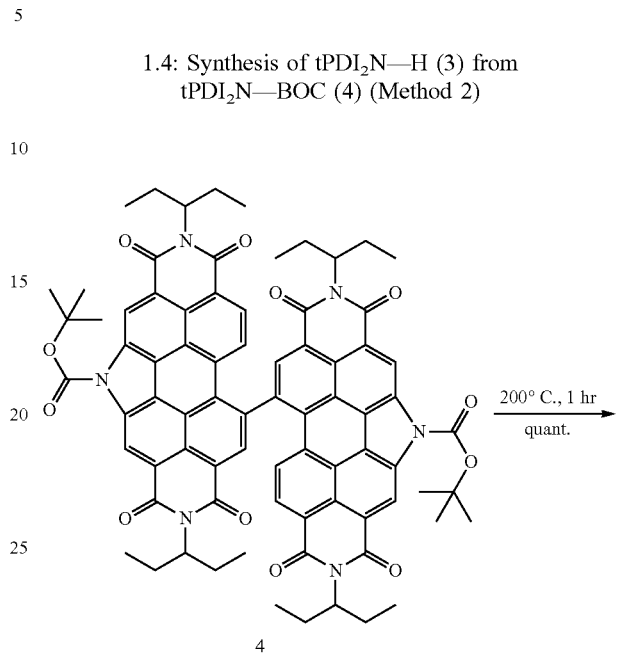

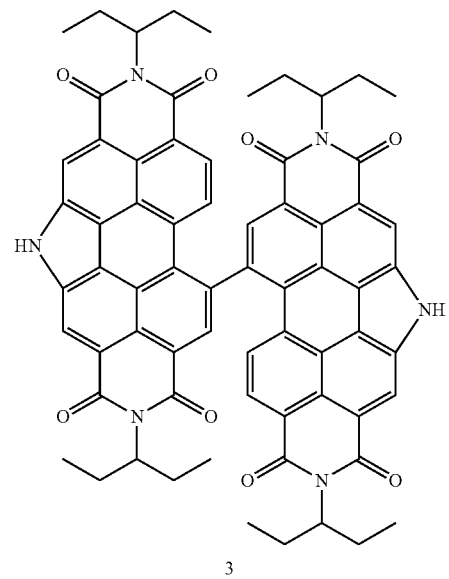

Synthesis of tPDI₂N—H Dimer (3) by Heating tPDI₂N—BOC Dimer (4) to 200° C. for 1 Hour tPDI₂N—BOC dimer (4) was placed in a glass vial and heated in a vacuum oven at 200° C. for 1 hour which resulted in quantitative conversion to the tPDI₂N—H dimer (3). Spectroscopic features were identical to that of 3 prepared from 2.

1.5: Synthesis of BrPDIN-BOC (6)

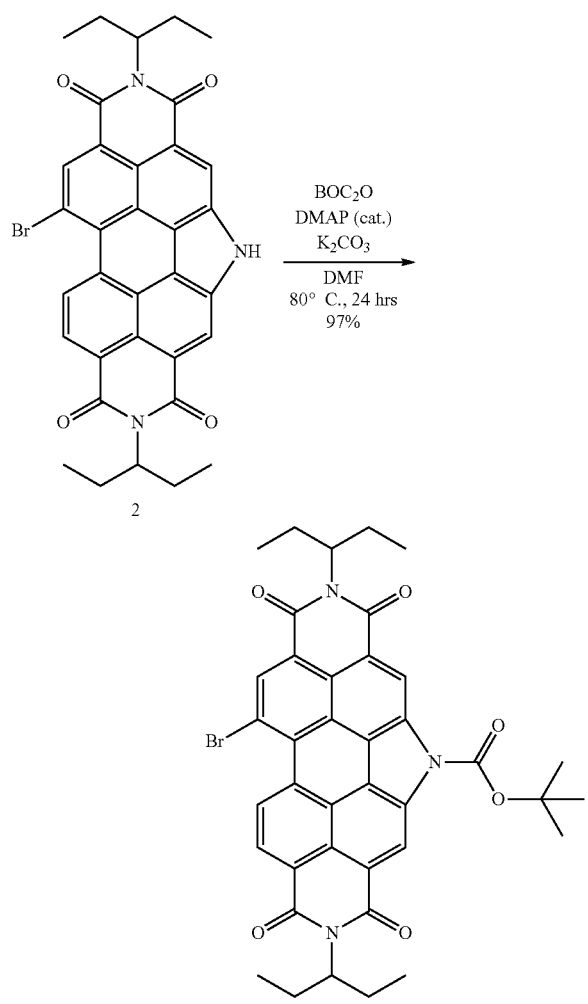

Synthesis of BrPDIN-BOC (6)

BrPDIN-H (2) (1.00 g, 1.61 mmol, 1.00 eq.) and 4-dimethylaminopyridine (DMAP) (32 mg, 0.262 mmol, 0.16 eq.) were added to a 250-mL round bottom flask containing a magnetic stir bar and dry DMF (90 mL) was added via cannula transfer. The head space of the flask was purged with $N_2$ gas for 10 minutes and di-tert-butyl dicarbonate ($BOC_2O$) (0.947 g, 1.00 mL, 4.34 mmol, 2.70 eq.) was added via syringe. The solution was heated to 80° C. and was reacted for 2 hours while stirring. This caused the yellow solution to become red and opaque. Following this, the septa was removed quickly, potassium carbonate (0.251 g, 1.82 mmol, 1.13 eq.) was added, the flask was resealed and the solution was left to react. After 2 additional hours, TLC measurements indicated complete consumption of the starting material. The solution was cooled to room temperature and concentrated under reduced pressure using a rotary evaporator. The rotary evaporator bath should not be hotter than 60° C. to avoid thermal deprotection of the BOC group. The residue was taken up in dichloromethane (100 mL) and extracted using $H_2O$ (1×50 mL) and brine (1×50 mL). The organic phase was dried over $MgSO_4$, passed through a 1-inch silica plug and concentrated under reduced pressure using a rotary evaporator. The resulting solid was slurried in methanol (100 mL) and vacuum filtered to yield a red, opaque solid (1.11 g, 97%). $^1$H NMR (Chloroform-d, TMS/ppm) δ: 10.12 (d, 1H), 9.37 (bs, 2H), 9.01 (s, 1H), 8.84 (d, 1H), 5.19 (m, 2H), 2.33 (m, 4H), 2.02 (m, 4H), 1.97 (bs, 9H), 0.99 (q, 12H). $^{13}$C NMR (ppm): 149.1, 131.7, 124.6, 122.8, 119.9, 119.8, 86.4, 57.4, 35.9, 30.9, 27.7, 24.6, 11.1. MS (APCI): expected 724.18, found 724.19.

1.6: Synthesis of tPDI$_2$N—BOC (4) from BrPDIN-BOC (6) (Method 2)

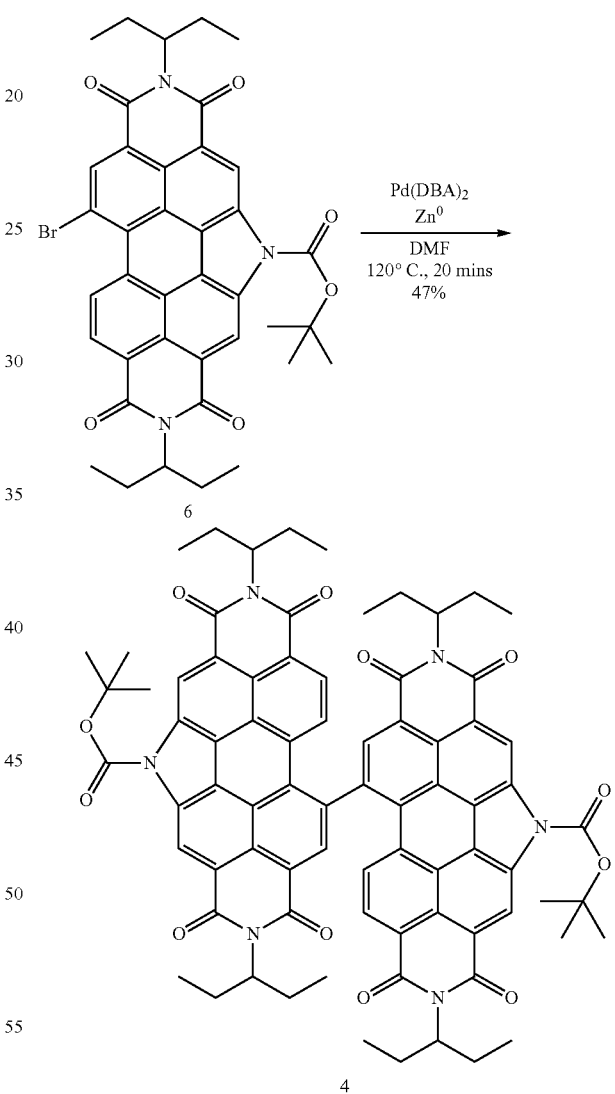

Synthesis of tPDI$_2$N—BOC (4) through Negishi-type coupling of BrPDIN-BOC (6)

Method 2:

BrPDIN-BOC (6) (460 mg, 0.636 mmol, 1.00 eq.), bis(dibenzylideneacetone) palladium(0) (44 mg, 0.076 mmol, 12 mol %) and zinc dust (204 mg, 3.20 mmol, 4.90 eq.) were all added to a 100-mL round bottomed flask equipped with a magnetic stir bar. The head space of the flask was purged with N₂ gas for 10 minutes and then dry DMF (40 mL) was added via cannula transfer. The solution was heated to 120° C. while stirring. After 10 minutes, the solution changed from a deep red to a dark blue. After reacting for an additional 10 minutes, TLC measurements indicated completion of the reaction. The solution was cooled to room temperature, poured into dichloromethane (200 mL), passed through a 1-inch silica plug and then concentrated under reduced pressure using a rotary evaporator. The rotary evaporator bath should not be hotter than 60° C. to avoid thermal deprotection of the BOC group. The resulting solid was taken up in methanol (100 mL) and vacuum filtered to yield a fine, dark red powder (384 mg, 47%).

1.7: Synthesis of tPDI₂N-Hex (5) from tPDI₂N—H

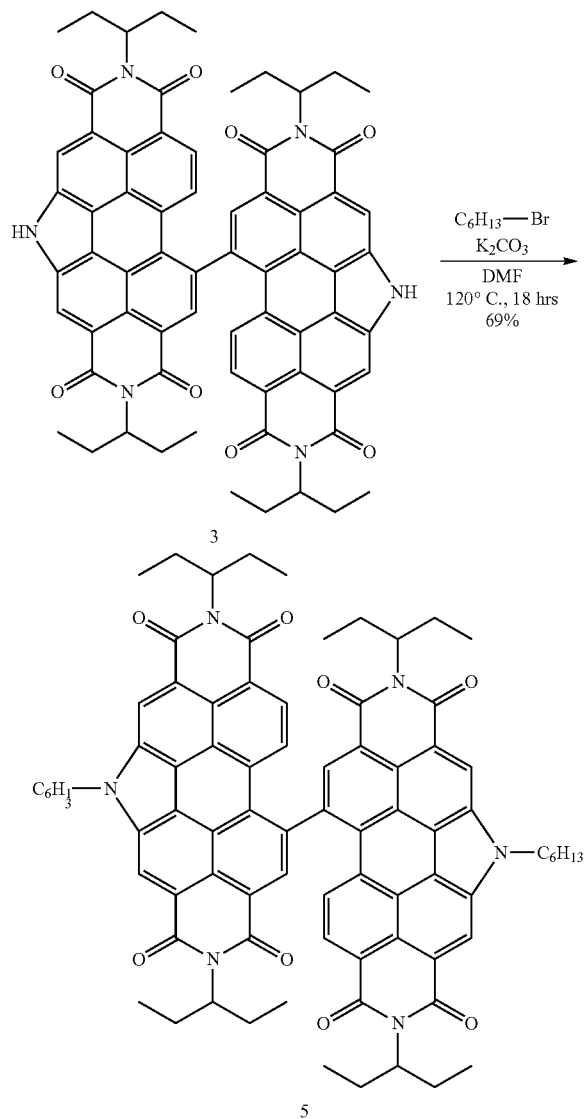

Synthesis of tPDI₂N-Hex Dimer (5)

tPDI₂N—H (3) (65 mg, 0.06 mmol, 1.00 eq.) and potassium carbonate (22 mg, 0.216 mmol, 3.60 eq.) were placed in a 10-mL microwave vial affixed with a magnetic stir bar. The vial was capped, the headspace was purged with N₂ gas for 10 minutes and dry DMF was added using a cannula transfer. The head space of the vial was purged for 10 minutes following addition of the solvent and 1-bromohexane was added via syringe, followed again by an N₂ purge of the head space for 5 minutes. The vial was heated to 120° C., causing the color to change from red to a dark purple. After 18 hours, the solution had converted back to a red color and was cooled to room temperature after TLC indicated complete consumption of the starting material. The solution was poured into dichloromethane (50 mL), placed in a separatory funnel and extracted using water (1×50 mL) and brine (1×50 mL). The organic phase was then collected, dried over MgSO₄, filtered through a 1-inch Celite plug and concentrated under reduced pressure on a rotary evaporator. The residue was taken up in methanol (25 mL) and vacuum filtered to yield the title product as a red, fine powder (52 mg, 69%). Spectroscopic data was identical to that previously reported. ¹H NMR (Chloroform-d, TMS/ppm) δ: 9.28 (s, 2H), 9.10 (s, 2H), 8.89 (s, 2H), 7.98 (s, 2H), 7.73-7.69 (m, 2H), 5.35-4.95 (m, 8H), 2.35-2.30 (m, 8H), 2.27-2.11 (m, 4H), 2.03-2.97 (m, 4H), 1.88-1.82 (m, 4H), 1.58-1.56 (m, 4H), 1.48-1.41 (m, 4H), 1.39-1.34 (m, 4H), 1.03-0.73 (m, 30H). MS (APCI): expected 1253.61, found 1253.84.

Example 2: Properties of Dimer 3 and Comparison to Dimers 4 and 5

The synthesis of tPDI₂N—H (3) is shown in Scheme 1 and described in Example 1. The N-annulated PDI monomer, PDIN-H (1), was brominated at the bay position to give the mono-brominated product BrPDIN-H (2). The bromination was found initially to proceed with excess Br₂ in refluxing CHCl₃ for 3 days using a catalytic amount of Fe, giving compound 2 in yields upwards of 90%. Because of the very low solubility of compound 1 in CHCl₃, an alternative method was employed in which the bromination was carried out in neat Br₂ within hours at room temperature giving quantitative yields. Compound 2 was dimerized using a palladium-catalyzed Negishi-type coupling to yield the target molecule 3 in yields upwards of 60%. This homocoupling proceeded smoothly within 30 minutes at 120° C. in dimethylformamide (DMF). Alternatively, compound 3 was synthesized by first installing an amine protecting group, e.g., tert-butyloxycarbonyl (BOC), at the pyrrolic nitrogen position of compound 2, followed by dimerization to form compound 4 and thermal deprotection to remove the protecting group and generate compound 3.

While increasing the number of steps, the use of the protecting group dramatically improved the solubility of the PDI compounds making them easier to work with. The PDI dimers tPDI₂N—BOC (4) and tPDI₂N-Hex (5) were synthesized from compound 3 to demonstrate the ease of dimer functionalization, to create highly soluble derivatives, and to allow for comparison to compound 3 to assess the impact of the N—H moiety on materials properties.

In the characterization of compound 3, diagnostic N—H resonances and stretches were observed at ~10 ppm ¹H NMR spectrum (FIG. 1) and ~3100-3400 cm-1 in the IR spectrum (not shown), respectively. Compound 5 has been previously described in US patent publication 20170352812, but was synthesized therein by alkylation of the monomer followed by dimerization. Compound 5 exhibits very high solubility (>50 mg/mL) in organic solvents such as CHCl₃ and C₆H₅Cl. Compound 4 is equally as soluble as compound 5 likely owing to the presence of the protecting group, large BOC organic fragments. In contrast, dimer 3 was found to be only sparingly soluble in $CHCl_3$ with solubility of approximate 5 mg/mL. The absence of alkyl chains and possible NH . . . O intermolecular bonding are believed responsible for the lower solubility of compound 3 in organic solvent. Further analysis by concentration dependent $^1H$ NMR spectroscopy (not shown) showed a significant downfield shift of the pyrrolic NH resonance and minor downfield shifts of the CH resonances of compound 3 upon increasing solution concentration suggesting aggregation of the PDI dimers through a NH interaction. No changes were observed in analogous experiments carried out with compound 5.

Figure 2A:
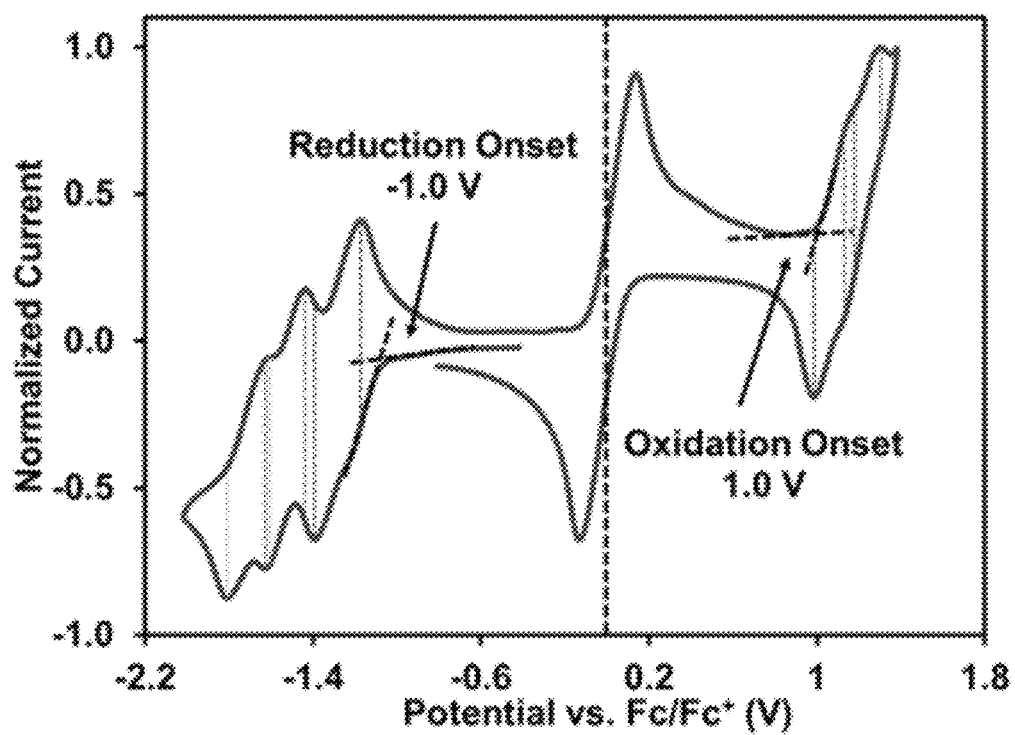
FIGS. 2A and 2B are normalized cyclic voltammetry (CV) plots of compounds 3 and 4, respectively, measured in dichloromethane solution.
Figure 2B:
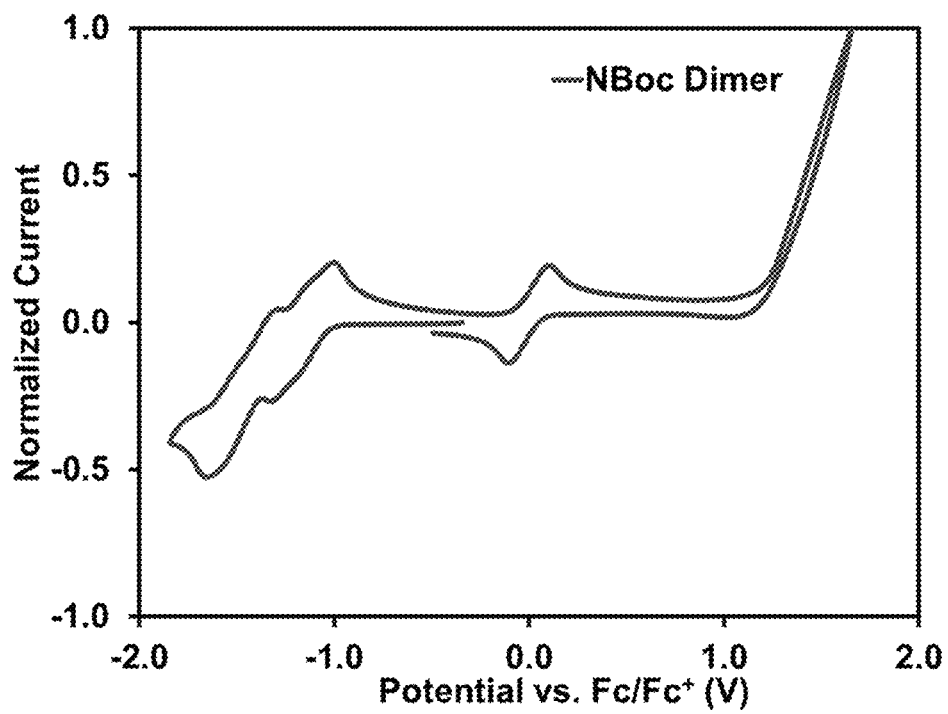

Compound 3 exhibits reversible ambipolar redox behavior (FIG. 2A, normalized CV plot of compound 3 in a dichloromethane solution using n-butylammonium hexafluorophosphate as an electrolyte. There are three identifiable reduction waves with $E_{1/2}$ values of −1.3, −1.5, and −1.7V vs. Fc/Fc$^+$. These are typical of dimeric PDI materials attributed to the electron deficient polycyclic aromatic backbones. Two reversible oxidation waves are observed with an $E_{1/2}$ at 1.1 and 1.2V vs. Fc/Fc$^+$. The oxidation is unique to the N-annulated PDI materials and attributed to the more electron rich pyrrolic rings. The electron affinity, 3.8 eV, and ionization potential, 5.8 eV, were determined from the onset of reduction (ca. −1.0V) and oxidation (ca. 1.0V), respectively, using a conversion value of 4.8. These values are similar to those of previously reported PDI dimers and indicate that compound 3 is suitable for use as an electron acceptor and transporting material in organic electronic devices. An analogous normalized CV plot of compound 4 is provided in FIG. 2B, where no oxidation is observed due to the electron withdrawing nature of the BOC group.

Compound 3 has strong optical absorption in the visible region of the spectrum, characteristic of PDI based materials (FIG. 3). The solution spectrum displays a strong band for the 0-0 transition at ~530 nm, and subsequently weaker bands at ~485 and ~455 nm corresponding to the 0-1 and 0-2 vibronic transitions, respectively. A transition from solution to film results in a bathochromic shift of the spectrum, but almost no change in the optical profile. Compared to compound 5, the higher energy band attributed to the 0-2 vibronic transition is more pronounced.

Figure 4A:
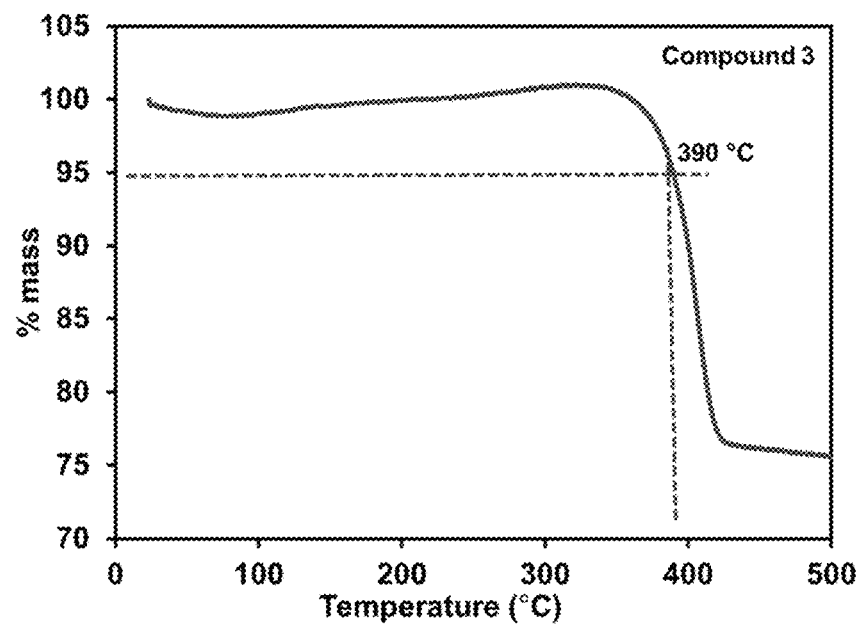
FIGS. 4A and B are Thermogravimetric Analysis (TGA) plots of compounds 3 and 4, respectively.
Figure 4B:
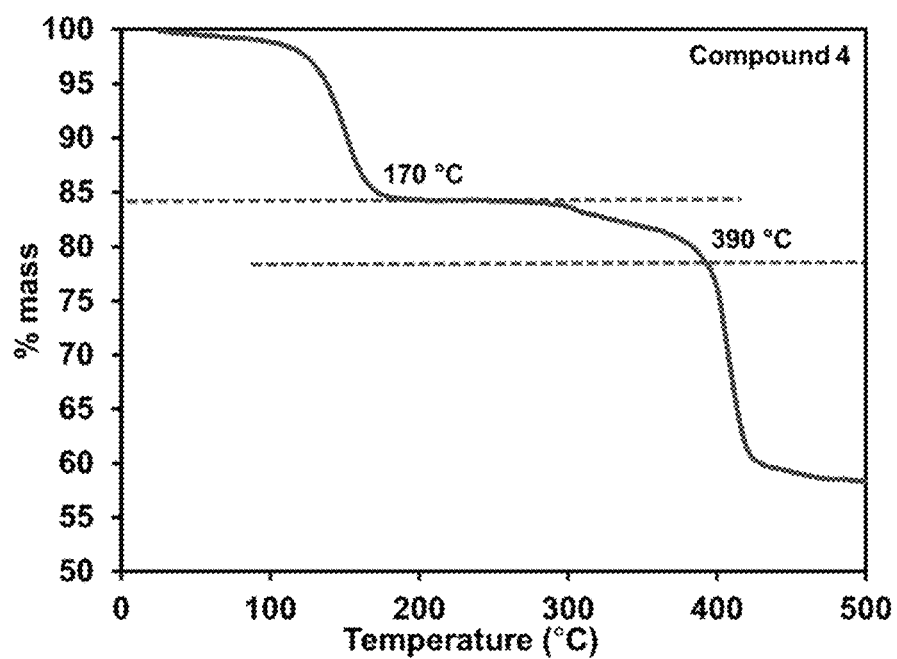

Compound 3 was found to be quite thermally stable. Decomposition occurred above 390° C. as determined by thermal gravimetric analysis (TGA, FIG. 4A) and no phase transitions were observed up to 350° C. as determined by differential scanning calorimetry (DSC) (see FIG. 5A). This stability is similar to that of compound 5. TGA of compound 4 is illustrated in FIG. 4B. The TGA were run under $N_2$ at 2° C. per min.

Figure 5A:
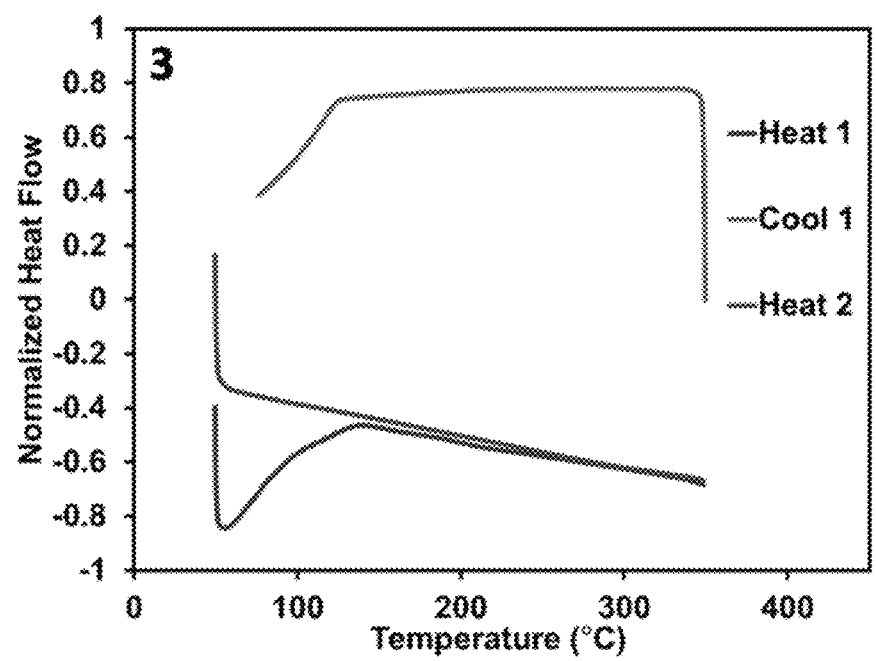
Figure 5B:
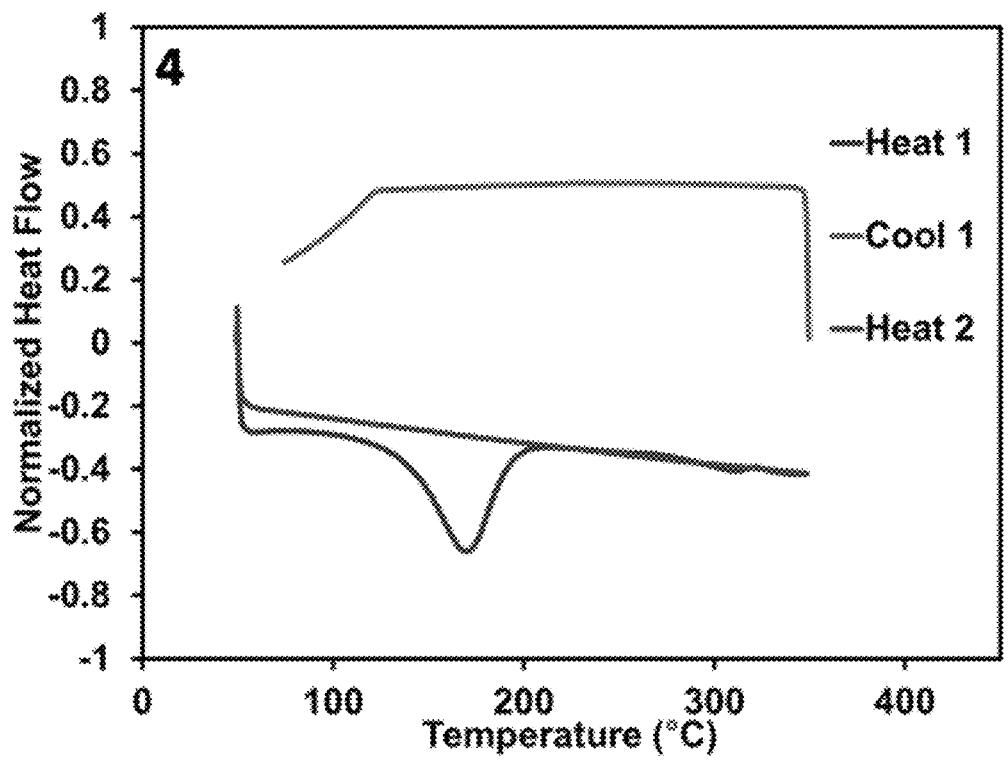
Figure 5C:
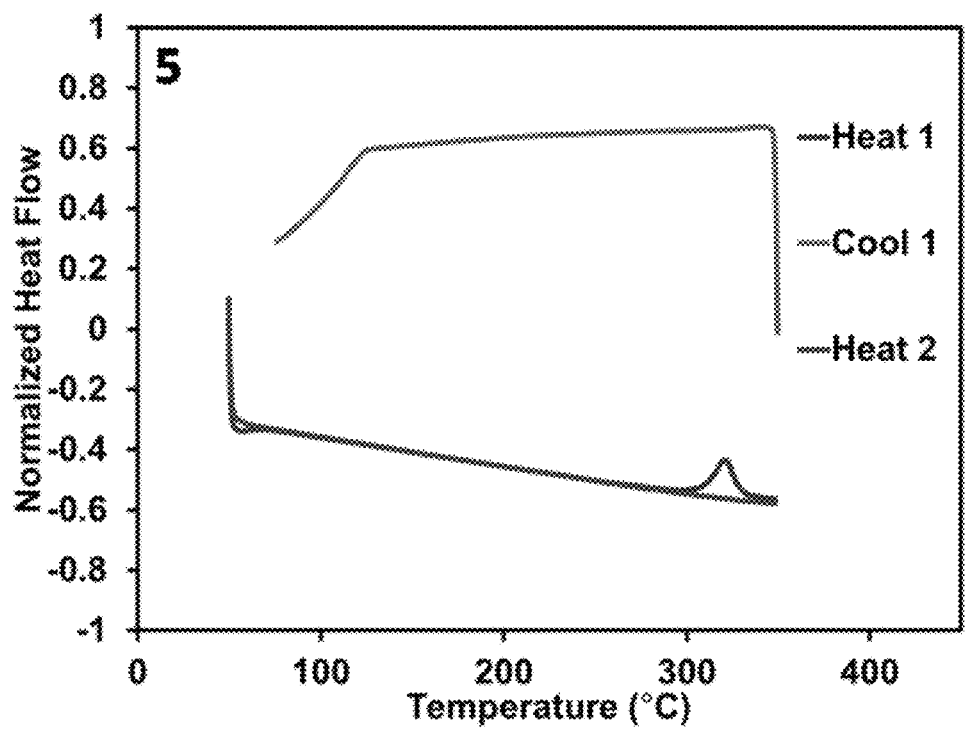

The impact of thermal annealing on the thin-film optical absorption profile is an important factor for use of such dimers. The BOC functionalized derivative 4 was synthesized at least in part to enable facile solution processing of the PDI dimer and generation of 3 in the solid film through thermal deprotection after film formation. FIGS. 5A-5C are DSC plots for compounds 3, 4 and 5, respectively, run under $N_2$ at 10° C. per min. For clarity, the second and third trials of each cooling run and the third trial of each heating run is omitted for all species because the data is indistinguishable from previous runs. During the first heating trial of compound 4, an endothermic peak is clearly present in the plot with an onset occurring at 160° C. This was assumed to be the temperature where cleavage of the protecting group begins to occur and this is confirmed by the fact that this feature is not present in the second heating trial, which has a profile strongly resembling that of the heated NH Dimer 3 and further confirmed by bulk deprotection of compound 4 in an oven at 180° C. The first heating trial of compound 3 features a smooth, downward sloping line. The first heating trial of compound 5 also showed a steadily decreasing line, but with a small exothermic peak close to the end (325° C.). This feature is due to a cold-crystallization and has previously been observed in similar molecules.

Analysis by both TGA (FIG. 4B) and DSC (FIG. 5B) shows the loss of the BOC group from compound 4 at ~170° C. Thus, films were thermally annealed above this temperature (e.g., at 200° C.) to ensure the BOC protecting group was removed. Films of all three compounds 3-5 were studied.

Figure 6A:
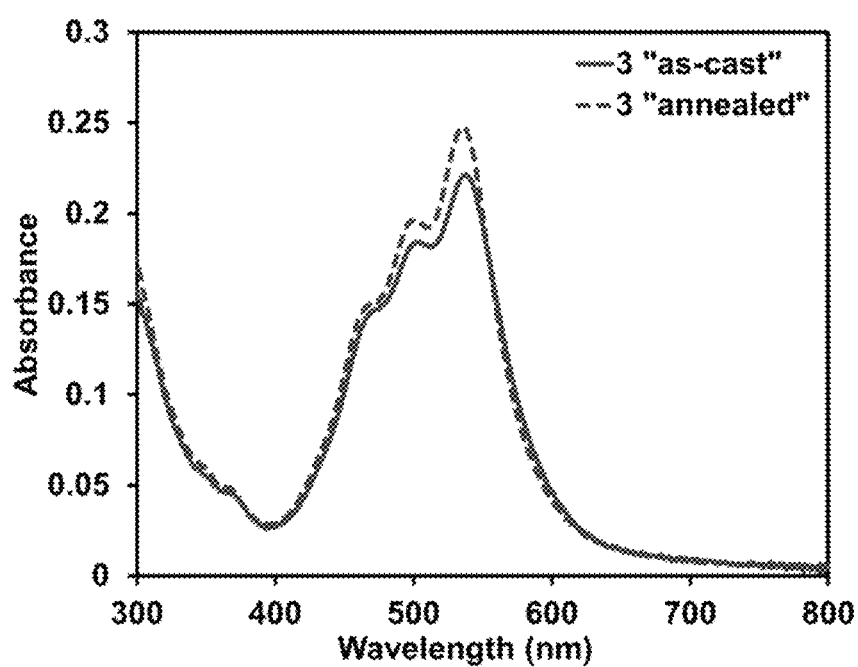
FIGS. 6A, 6B and 6C are optical absorption spectra of compounds 3, 4 and 5, respectively as cast films, before and after thermal annealing at 200 C for 10 minutes.
Figure 6B:
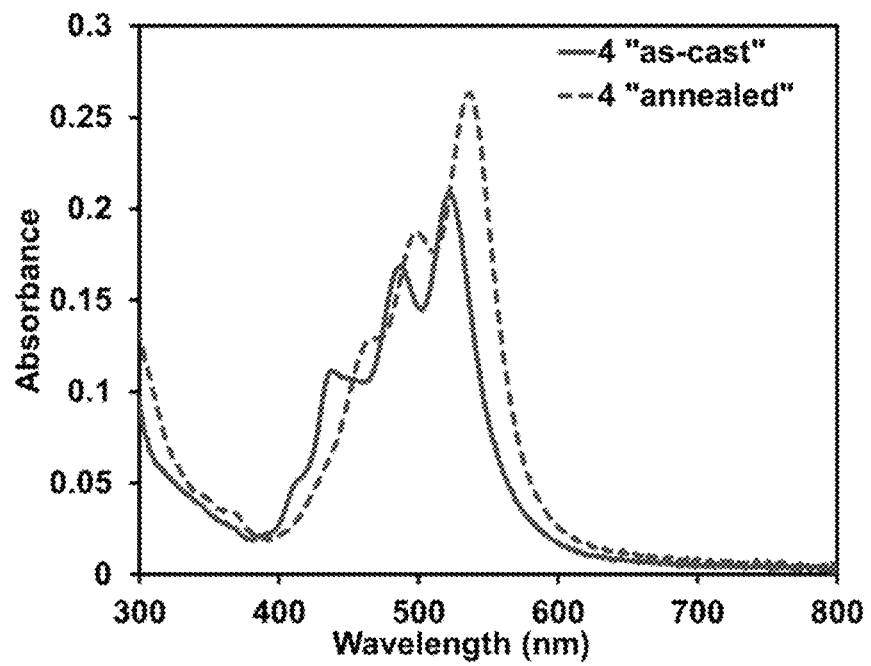
Figure 6C:
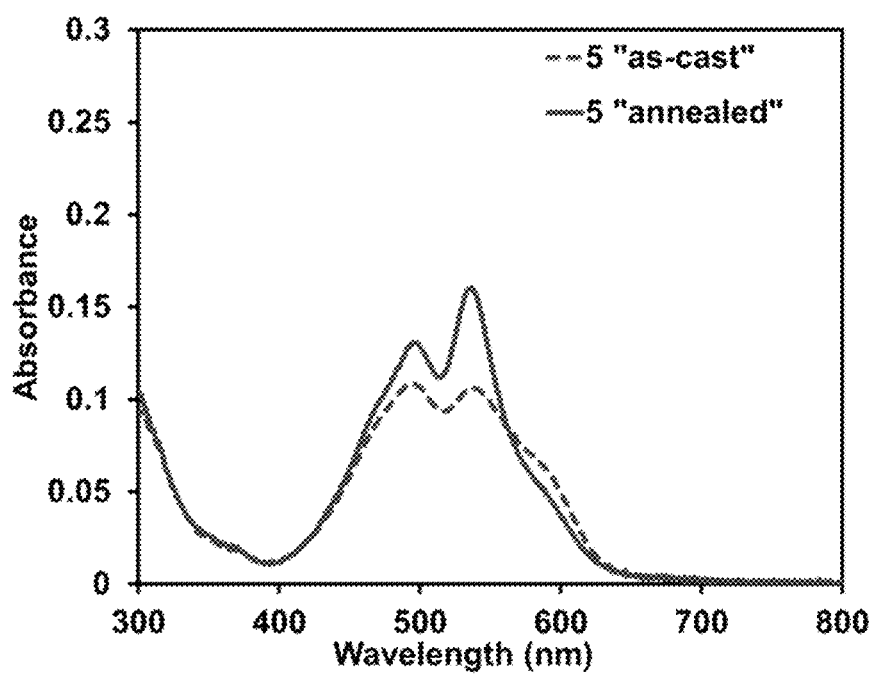

FIGS. 6A to 6C illustrate optical absorption spectra of compounds 3, 4 and 5, respectively as thin films. Films were cast from 5 mg/mL, 10 mg/mL and 10 mg/mL chloroform, respectively, for compounds 3, 4, and 5. Films were measured "as-cast" and after being "annealed" (thermal annealing at 200° C. for 10 minutes). Thermal annealing a film of compound 3 results in no visible change to the film and no change in the optical absorption profile.

Cyclic Voltammetry (CV): All electrochemical measurements were performed using a CH Instruments potentiostat in a standard three-electrode configuration equipped with a silver wire pseudo-reference, platinum wire counter electrode and glassy carbon working electrode. The cyclic voltammetry experiments were performed in an anhydrous solution of dichloromethane ($CH_2Cl_2$) with ~0.1 M tetrabutylammonium-hexafluorophosphate (TBAPF$_6$) supporting electrolyte. Samples were scanned at a rate of 100 mV/s following a dry $N_2$ purge to deoxygenate the solution, unless otherwise noted. Solution CV measurements were carried out with a sample concentration of ~0.5 mg/mL in $CH_2Cl_2$, unless otherwise noted. Estimations of the energy levels were obtained by correlating the onset ($E_{ox}$ Fc/Fc+, $E_{red}$ Fc/Fc+) to the normal hydrogen electrode (NHE), assuming a HOMO energy level of 4.80 eV for Fc/Fc+:

$$E(HOMO)=-(E_{ox}+4.80), E(LUMO)=-(E_{red}+4.80)$$

UV-Visible Spectroscopy (UV/vis): All absorption measurements were recorded using an Agilent Technologies Cary 60 UV-vis spectrometer at room temperature. All solution UV/vis experiments were run in chloroform ($CHCl_3$) using 2 mm quartz cuvettes and diluted 1% wt/v solutions, unless otherwise noted. Thin-films were prepared by spin-coating 1% wt/v solutions from $CHCl_3$ onto Corning glass micro slides, unless otherwise noted. Prior to use, glass slides were cleaned with soap and water, acetone and isopropanol, and followed by UV/ozone treatment using a Novascan UV/ozone cleaning system.

REFERENCES (1) Zhan, X.; Facchetti, A.; Barlow, S.; Marks, T. J.; Ratner, M. A.; Wasielewski, M. R.; Marder, S. R. Rylene and Related Diimides for Organic Electronics. Adv. Mater. 2011, 23, 268-284.

(2) Zhong, Y.; Trinh, M. T.; Chen, R.; Purdum, G. E.; Khlyabich, P. P.; Sezen, M.; Oh, S.; Zhu, H.; Fowler, B.; Zhang, B.; Wang, W.; Nam, C.-Y.; Sfeir, M. Y.; Black, C. T.; Steigerwald, M. L.; Loo, Y.-L.; Ng, F.; Zhu, X.-Y.; Nuckolls, C. Molecular Helices as Electron Acceptors in High-Performance Bulk Heterojunction Solar Cells. Nat. Commun. 2015, 6, 8242.

(3) Meng, D.; Sun, D.; Zhong, C.; Liu, T.; Fan, B.; Huo, L.; Li, Y.; Jiang, W.; Choi, H.; Kim, T.; Kim, J. Y.; Sun, Y.; Wang, Z.; Heeger, A. J. High-Performance Solution-Processed Non-Fullerene Organic Solar Cells Based on Selenophene-Containing Perylene Bisimide Acceptor. J. Am. Chem. Soc. 2016, 138, 375-380.

(4) Zhong, Y.; Trinh, M. T.; Chen, R.; Wang, W.; Khlyabich, P. P.; Kumar, B.; Xu, Q.; Nam, C.-Y.; Sfeir, M. Y.; Black, C.; Steigerwald, M. L.; Loo, Y.-L.; Xiao, S.; Ng, F.; Zhu, X.-Y.; Nuckolls, C. Efficient Organic Solar Cells with Helical Perylene Diimide Electron Acceptors. J. Am. Chem. Soc. 2014, 136, 15215-15221.

(5) Liu, K.; Xu, Z.; Yin, M.; Yang, W.; He, B.; Wei, W.; Shen, J. A Multifunctional Perylenediimide Derivative (DTPDI) Can Be Used as a Recyclable Specific Hg2+ Ion Sensor and an Efficient DNA Delivery Carrier. J. Mater. Chem. B 2014, 2, 2093-2096.

(6) Dwivedi, A. K.; Pandeeswar, M.; Govindaraju, T. Assembly Modulation of PDI Derivative as a Supramolecular Fluorescence Switching Probe for Detection of Cationic Surfactant and Metal Ions in Aqueous Media. ACS Appl. Mater. Interfaces 2014, 6, 21369-21379.

(7) Doval, D. A.; Fin, A.; Takahashi-Umebayashi, M.; Riezman, H.; Roux, A.; Sakai, N.; Matile, S. Amphiphilic Dynamic NDI and PDI Probes: Imaging Microdomains in Giant Unilamellar Vesicles. Org. Biomol. Chem. 2012, 10, 6087-6093.

(8) Acikbas, Y.; Erdogan, M.; Capan, R.; Yukruk, F. OpticalC haracterization of an N, N'-Dicyclohexyl-3, 4:9, 10-Perylene bis(Dicarboximide) Langmuir-Blodgett Film for the Determination of Volatile Organic Compounds. Anal. Lett. 2016, DOI: 10.1080/00032719.2015.1122028.

(9) Hariharan, P. S.; Pitchaimani, J.; Madhu, V.; Anthony, S. P. Perylene Diimide Based Fluorescent Dyes for Selective Sensing of Nitroaromatic Compounds: Selective Sensing in Aqueous Medium Across Wide pH Range. J. Fluoresc. 2016, 26, 395-401.

(10) Huang, Y.; Zhang, W.; Wang, J.; Wei, Z. Probing the Sensory Property of Perylenediimide Derivatives in Hydrazine Gas: Core-Substituted Aromatic Group Effect. ACS Appl. Mater. Interfaces 2014, 6, 9307-9313.

(11) Feng, X.; An, Y.; Yao, Z.; Li, C.; Shi, G. A Turn-on Fluorescent Sensor for Pyrophosphate Based on the Disassembly of Cu2+-Mediated Perylene Diimide Aggregates. ACS Appl. Mater. Interfaces 2012, 4, 614-618.

(12) Hüttner, S.; Sommer, M.; Thelakkat, M. N-Type Organic Field Effect Transistors from Perylene Bisimide Block Copolymers and Homopolymers. Appl. Phys. Lett. 2008, 92, 093302.

(13) Lüttich, F.; Lehmann, D.; Friedrich, M.; Chen, Z.; Facchetti, A.; Borczyskowski, C.; von Zahn, D. R. T.; Graaf, H. Interface Properties of OFETs Based on an Air-Stable N-Channel Perylene Tetracarboxylic Diimide Semiconductor. Phys. Status Solidi A 2012, 209, 585-593.

(14) Centore, R.; Ricciotti, L.; Carella, A.; Roviello, A.; Causà, M.; Barra, M.; Ciccullo, F.; Cassinese, A. Perylene Diimides Functionalized with N-Thiadiazole Substituents: Synthesis and Electronic Properties in OFET Devices. Org. Electron. 2012, 13, 2083-2093.

(15) Tilley, A. J.; Guo, C.; Miltenburg, M. B.; Schon, T. B.; Yan, H.; Li, Y.; Seferos, D. S. Thionation Enhances the Electron Mobility of Perylene Diimide for High Performance N-Channel Organic Field Effect Transistors. Adv. Funct. Mater. 2015, 25, 3321-3329.

(16) Kozma, E.; Catellani, M. Perylene Diimides Based Materials for Organic Solar Cells. Dyes Pigm. 2013, 98, 160-179.

(17) Fernandez-Lazaro, F.; Zink-Lorre, N.; Sastre-Santos, A. Perylenediimides as Non-Fullerene Acceptors in Bulk-Heterojunction Solar Cells (BHJSCs). J. Mater. Chem. A 2016, 4, 9336-9346.

(18) Hartnett, P. E.; Timalsina, A.; Matte, H. S. S. R.; Zhou, N.; Guo, X.; Zhao, W.; Facchetti, A.; Chang, R. P. H.; Hersam, M. C.; Wasielewski, M. R.; Marks, T. J. Slip-Stacked Perylenediimides as an Alternative Strategy for High Efficiency Nonfullerene Acceptors in Organic Photovoltaics. J. Am. Chem. Soc. 2014, 136, 16345-16356.

(19) Jiang, W.; Ye, L.; Li, X.; Xiao, C.; Tan, F.; Zhao, W.; Hou, J.; Wang, Z. Bay-Linked Perylene Bisimides as Promising Non-Fullerene Acceptors for Organic Solar Cells. Chem. Commun. 2014, 50, 1024-1026.

(20) Su, Y.-W.; Lan, S.-C.; Wei, K.-H. Organic Photovoltaics. Mater. Today 2012, 15, 554-562.

(21) Li, G.; Zhu, R.; Yang, Y. Polymer Solar Cells. Nat. Photonics 2012, 6, 153-161.

(22) Roncali, J.; Leriche, P.; Blanchard, P. Molecular Materials for Organic Photovoltaics: Small Is Beautiful. Adv. Mater. 2014, 26, 3821-3838.

(23) Lin, Y.; Zhan, X. Non-Fullerene Acceptors for Organic Photovoltaics: An Emerging Horizon. Mater. Horiz. 2014, 1, 470-488.

(24) Eftaiha, A. F.; Sun, J.-P.; Hill, I. G.; Welch, G. C. Recent Advances of Non-Fullerene, Small Molecular Acceptors for Solution Processed Bulk Heterojunction Solar Cells. J. Mater. Chem. A 2014, 2, 1201-1213.

(25) Chochos, C. L.; Tagmatarchis, N.; Gregoriou, V. G. Rational Design on N-Type Organic Materials for High Performance Organic Photovoltaics. RSC Adv. 2013, 3, 7160-7181.

(26) Anthony, J. E. Small-Molecule, Nonfullerene Acceptors for Polymer Bulk Heterojunction Organic Photovoltaics. Chem. Mater. 2011, 23, 583-590.

(27) Zhan, C.; Zhang, X.; Yao, J. New Advances in Non-Fullerene Acceptor Based Organic Solar Cells. RSC Adv. 2015, 5, 93002-93026.

(28) McAfee, S. M.; Topple, J. M.; Hill, I. G.; Welch, G. C. Key Components to the Recent Performance Increases of Solution Processed Non-Fullerene Small Molecule Acceptors. J. Mater. Chem. A 2015, 3, 16393-16408.

(29) Zhan, C.; Yao, J. More than Conformational "Twisting" or "Coplanarity": Molecular Strategies for Designing High-Efficiency Nonfullerene Organic Solar Cells. Chem. Mater. 2016, 28, 1948-1964.

(30) Lin, Y.; Wang, J.; Dai, S.; Li, Y.; Zhu, D.; Zhan, X. A Twisted Dimeric Perylene Diimide Electron Acceptor for Efficient Organic Solar Cells. Adv. Energy Mater. 2014, 4, 1400420.

(31) Lin, Y.; Wang, Y.; Wang, J.; Hou, J.; Li, Y.; Zhu, D.; Zhan, X. A Star-Shaped Perylene Diimide Electron Acceptor for High-Performance Organic Solar Cells. Adv. Mater. 2014, 26, 5137-5142.

(32) Chen, W.; Yang, X.; Long, G.; Wan, X.; Chen, Y.; Zhang, Q. A Perylene Diimide (PDI)-Based Small Molecule with Tetrahedral Configuration as a Non-Fullerene Acceptor for Organic Solar Cells. J. Mater. Chem. C 2015, 3, 4698-4705.

(33) Zhan, X.; Tan, Z.; Domercq, B.; An, Z.; Zhang, X.; Barlow, S.; Li, Y.; Zhu, D.; Kippelen, B.; Marder, S. R. A High-Mobility Electron-Transport Polymer with Broad Absorption and Its Use in Field-Effect Transistors and All-Polymer Solar Cells. J. Am. Chem. Soc. 2007, 129, 7246-7247.

(34) Liu, X.; Luo, G.; Cai, X.; Wu, H.; Su, S.-J.; Cao, Y. Pyrene Terminal Functionalized Perylene Diimide as Non-Fullerene Acceptors for Bulk Heterojunction Solar Cells. RSC Adv. 2015, 5, 83155-83163.

(35) Yan, Q.; Zhou, Y.; Zheng, Y.-Q.; Pei, J.; Zhao, D. Towards Rational Design of Organic Electron Acceptors for Photovoltaics: A Study Based on Perylenediimide Derivatives. Chem. Sci. 2013, 4, 4389-4394.

(36) Sun, D.; Meng, D.; Cai, Y.; Fan, B.; Li, Y.; Jiang, W.; Huo, L.; Sun, Y.; Wang, Z. Non-Fullerene Acceptor-Based Bulk Heterojunction Organic Solar Cells with Efficiency over 7%. J. Am. Chem. Soc. 2015, 137, 11156-11162.

(37) Zang, Y.; Li, C.-Z.; Chueh, C.-C.; Williams, S. T.; Jiang, W.; Wang, Z.-H.; Yu, J.-S.; Jen, A. K.-Y. Integrated Molecular, Interfacial, and Device Engineering towards High-Performance Non-Fullerene Based Organic Solar Cells. Adv. Mater. 2014, 26, 5708-5714.

(38) Demmig, S.; Langhals, H. Leichtlosliche, Lichtechte Perylen-Fluoreszenzfarbstoffe. Chem. Ber. 1988, 121, 225-230.

(39) Langhals, H.; Kirner, S. Novel Fluorescent Dyes by the Extension of the Core of Perylenetetracarboxylic Bisimides. Eur. J. Org. Chem. 2000, 2000, 365-380.

(40) Freeman, A. W.; Urvoy, M.; Criswell, M. E. Triphenylphosphine-Mediated Reductive Cyclization of 2-Nitrobiphenyls: A Practical and Convenient Synthesis of Carbazoles. J. Org. Chem. 2005, 70, 5014-5019.

(41) Marrocchi, A.; Facchetti, A.; Lanari, D.; Petrucci, C.; Vaccaro, L. Current Methodologies for a Sustainable Approach to [Capital Pi]-Conjugated Organic Semiconductors. Energy Environ. Sci. 2016, 9, 763-786.

(42) McAfee, S. M.; Cann, J. R.; Josse, P.; Blanchard, P.; Cabanetos, C.; Welch, G. C. The Optimization of Direct Heteroarylation and Sonogashira Cross-Coupling Reactions as Efficient and Sustainable Synthetic Methods to Access π-Conjugated Materials with Near-Infrared Absorption. ACS Sustainable Chem. Eng. 2016, 4, 3504-3517.

(43) McAfee, S. M.; McCahill, J. S. J.; Macaulay, C. M.; Hendsbee, A. D.; Welch, G. C. Utility of a Heterogeneous Palladium Catalyst for the Synthesis of a Molecular Semiconductor via Stille, Suzuki, and Direct Heteroarylation Cross-Coupling Reactions. RSC Adv. 2015, 5, 26097-26106.

(44) Burke, D. J.; Lipomi, D. J. Green Chemistry for Organic Solar Cells. Energy Environ. Sci. 2013, 6, 2053-2066.

(45) Rajasingh, P.; Cohen, R.; Shirman, E.; Shimon, L. J. W.; Rybtchinski, B. Selective Bromination of Perylene Diimides under Mild Conditions. J. Org. Chem. 2007, 72, 5973-5979.

(46) Hendsbee, A. D.; McAfee, S. M.; Sun, J.-P.; McCormick, T. M.; Hill, I. G.; Welch, G. C. Phthalimide-Based [Small Pi]-Conjugated Small Molecules with Tailored Electronic Energy Levels for Use as Acceptors in Organic Solar Cells. J. Mater. Chem. C 2015, 3, 8904-8915.

(47) Ding, L.; Li, H.-B.; Lei, T.; Ying, H.-Z.; Wang, R.-B.; Zhou, Y.; Su, Z.-M.; Pei, J. Alkylene-Chain Effect on Microwire Growth and Crystal Packing of π-Moieties. Chem. Mater. 2012, 24, 1944-1949.

(48) Anthony, J. E.; Eaton, D. L.; Parkin, S. R. A Road Map to Stable, Soluble, Easily Crystallized Pentacene Derivatives. Org. Lett. 2002, 4, 15-18.

(49) Fitzner, R.; Elschner, C.; Weil, M.; Uhrich, C.; Körner, C.; Riede, M.; Leo, K.; Pfeiffer, M.; Reinold, E.; Mena-Osteritz, E.; Bäuerle, P. Interrelation between Crystal Packing and Small-Molecule Organic Solar Cell Performance. Adv. Mater. 2012, 24, 675-680.

(50) Kim, C.; Liu, J.; Lin, J.; Tamayo, A. B.; Walker, B.; Wu, G.; Nguyen, T.-Q. Influence of Structural Variation on the Solid-State Properties of Diketopyrrolopyrrole-Based Oligophenylenethiophenes: Single-Crystal Structures, Thermal Properties, Optical Bandgaps, Energy Levels, Film Morphology, and Hole Mobility. Chem. Mater. 2012, 24, 1699-1709.

(51) Namepetra, A.; Kitching, E.; Eftaiha, A. F.; Hill, I. G.; Welch, G. C. Understanding the Morphology of Solution Processed Fullerene-Free Small Molecule Bulk Heterojunction Blends. Phys. Chem. Chem. Phys. 2016, 18, 12476-12485.

(52) Sun, J.-P.; Hendsbee, A. D.; Dobson, A. J.; Welch, G. C.; Hill, I. G. Perylene Diimide Based All Small-Molecule Organic Solar Cells: Impact of Branched-Alkyl Side Chains on Solubility, Photophysics, Self-Assembly, and Photovoltaic Parameters. Org. Electron. 2016, 35, 151-157.

(53) Qian, H.; Yue, W.; Zhen, Y.; Di Motta, S.; Di Donato, E.; Negri, F.; Qu, J.; Xu, W.; Zhu, D.; Wang, Z. Heterocyclic Annelated Di(perylene Bisimide): Constructing Bowl-Shaped Perylene Bisimides by the Combination of Steric Congestion and Ring Strain. J. Org. Chem. 2009, 74, 6275-6282.

(54) Forrest, S. R. The Path to Ubiquitous and Low-Cost Organic Electronic Appliances on Plastic. Nature 2004, 428, 911-918.

(55) Mei, J.; Bao, Z. Side Chain Engineering in Solution-Processable Conjugated Polymers. Chem. Mater. 2014, 26, 604-615.

(56) Li, M.; Liu, J.; Cao, X.; Zhou, K.; Zhao, Q.; Yu, X.; Xing, R.; Han, Y. Achieving Balanced Intermixed and Pure Crystalline Phases in PDI-Based Non-Fullerene Organic Solar Cells via Selective Solvent Additives. Phys. Chem. Chem. Phys. 2014, 16, 26917-26928.

(57) Chen, Z.; Stepanenko, V.; Dehm, V.; Prins, P.; Siebbeles, L. D. A.; Seibt, J.; Marquetand, P.; Engel, V.; Würthner, F. Photoluminescence and Conductivity of Self-Assembled Π-π Stacks of Perylene Bisimide Dyes. Chem.—Eur. J. 2007, 13, 436-449.

(58) Bredas, J.-L. Mind the Gap! Mater. Horiz. 2014, 1, 17-19.

(59) Cardona, C. M.; Li, W.; Kaifer, A. E.; Stockdale, D.; Bazan, G. C. Electrochemical Considerations for Determining Absolute Frontier Orbital Energy Levels of Conjugated Polymers for Solar Cell Applications. Adv. Mater. 2011, 23, 2367-2371.

(60) Li, J.; Dierschke, F.; Wu, J.; Grimsdale, A. C.; Mullen, K. Poly(2,7-Carbazole) and Perylene Tetracarboxydiimide: A Promising Donor/acceptor Pair for Polymer Solar Cells. J. Mater. Chem. 2006, 16, 96-100.

(61) Lu, L.; Yu, L. Understanding Low Bandgap Polymer PTB7 and Optimizing Polymer Solar Cells Based on It. Adv. Mater. 2014, 26, 4413-4430.

(62) Chang, L.; Jacobs, I. E.; Augustine, M. P.; Moulé, A. J. Correlating Dilute Solvent Interactions to Morphology and OPV Device Performance. Org. Electron. 2013, 14, 2431-2443.

(63) Liao, H.-C.; Ho, C.-C.; Chang, C.-Y.; Jao, M.-H.; Darling, S. B.; Su, W.-F. Additives for Morphology Control in High-Efficiency Organic Solar Cells. Mater. Today 2013, 16, 326-336.

(64) Chen, K.-Y.; Chow, T. J. "Highly Soluble Monoamino-Substituted Perylene Tetracarboxylic Dianhydrides: Synthesis, Optical and Electrochemical Properties," Tetrahedron Lett. 2010, 51 (45), 5959.

(65) Qiu, S.; Liu, L.; Wang, B.; Shen, F.; Zhang, W.; Li, M.; Ma, Y. Macromolecules 2005, 38 (16), 67.
(66) Hendsbee, A. D.; Sun, J-P.; Law W. K.; Yan, H.; Hill, I. G.; Denis M. Spasyuk, D. M. and Welch, G. C. Synthesis, Self-Assembly, and Solar Cell Performance of N-AnnulatedPerylene Diimide Non-Fullerene Acceptors. Chem. Mater, September 2016, 28, 7098-7109.
(67) McAfee, S. M.; Dayneko, S. V.; Josse, P.; Blanchard, P.; Cabanetos, C.; and Welch, G. C. Simply Complex: The Efficient Synthesis of an Intricate Molecular Acceptor for High-Performance Air-Processed and Air-Tested Fullerene-Free Organic Solar Cells, Chem. Mater., January 2017, 29, 1309-1314.
(68) Dayneko, S. V.; Hendsbee, A. D.; and Welch, G. C. Fullerene-free polymer solar cells processed from non-halogenated solvents in air with PCE of 4.8% Chem. Comm. 53, 1164-1167.
(69) Liao, S-H.; Jhuo, H.-J.; Cheng, Y.-S. and Chen, S.-A., Adv. Mater., 2013, 25, 4766-4771.
(70) Zhao, D.; Wu, Q.; Cai, Z.; Zheng, T.; Chen, W.; Lu J.; and Yu, L., Chem. Mater., 2016, 28, 1139-1146.
(71) Liu, Z.; Wu, Y.; Zhang, Q.; and Gao, X.; J. Mater. Chem. A, 2016, 4, 17604-17622.
(72) Zhan, C.; Yao, J. More than Conformational "Twisting" or "Coplanarity": Molecular Strategies for Designing High-Efficiency Nonfullerene Organic Solar Cells. Chem. Mater. 2016, 28, 1948-1964.
(73) Zhao, J.; Li, Y.; Lin, H.; Liu, Y.; Jiang, K.; Mu, C.; Ma, T.; Lai, J. Y. L.; Hu, H.; Yu, D.; Yan, H. High-Efficiency Non-Fullerene Organic Solar Cells Enabled by a Difluoro-benzothiadiazole-Based Donor Polymer Combined with a Properly Matched Small Molecule Acceptor. Energy Environ. Sci. 2015, 8, 520-525.
(74) Zhang, X.; Zhan, C.; Yao, J. Non-Fullerene Organic Solar Cells with 6.1% Efficiency through Fine-Tuning Parameters of the Film-Forming Process. Chem. Mater. 2015, 27, 166-173.
(75) Zhang, X.; Yao, J.; Zhan, C. A Selenophenyl Bridged Perylene Diimide Dimer as an Efficient Solution-Processable Small Molecule Acceptor. Chem. Commun. 2015, 51, 1058-1061.
(76) Zhang, X.; Li, W.; Yao, J.; Zhan, C. High-Efficiency Nonfullerene Polymer Solar Cell Enabling by Integration of Film-Morphology Optimization, Donor Selection, and Interfacial Engineering. ACS Appl. Mater. Interfaces 2016, 8, 15415-15421.
(77) Hendsbee, A. D.; Sun, J.-P.; Rutledge, L. R.; Hill, I. G.; Welch, G. C. Electron Deficient Diketopyrrolopyrrole Dyes for Organic Electronics: Synthesis by Direct Arylation, Optoelectronic Characterization, and Charge Carrier Mobility. J. Mater. Chem. A 2014, 2 (12), 4198-4207.
(78) Cann et al. (November 2017) Spectroscopic Engineering toward Near-Infrared Absorption of Materials Containing Perylene Diimide. ChemPlusChem 82(11) 1359-1364
(79) McAfee et al. (June 2017) A non-fullerene acceptor with a diagnostic morphological handle for streamlined screening of donor materials in organic solar cells J. Mater. Chem. A, 2017 5:16907-16913.
(80) Hendsbee et al. (March 2017)N-annulated perylene diimide dimers: the effect of thiophene bridges on physical, electronic, optical, and photovoltaic properties Sustainable Energy & Fuels 1:1137-1147.
(81) McAfee et al. (February 2017) Applying direct heteroarylation synthesis to evaluate organic dyes as the core component in PDI-based molecular materials for fullerene-free organic solar cells J. Mater. Chem. A, 2017 5, 11623-116.

We claim:

1. A compound of formula:

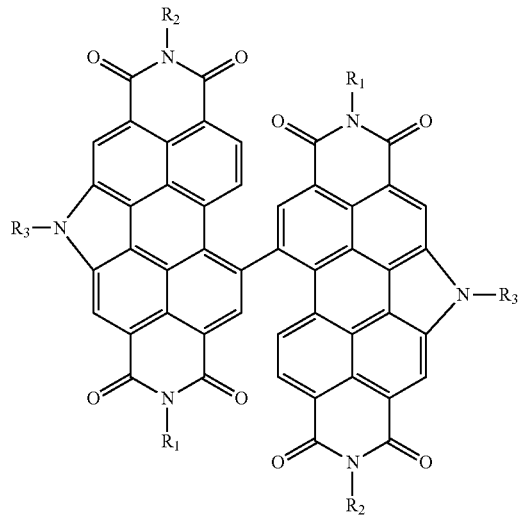

and salts thereof
where:
$R_1$ and $R_2$ are the same or different and are independently selected from straight-chain and branched alkyl groups having 1-30 carbon atoms; and
  (1) both $R_3$ are hydrogen; or
  (2) each $R_3$ is the same group or different groups and both are independently selected from amine protecting groups; or
  (3) each $R_3$ is the same group or different groups and each $R_3$ is independently selected from halogenated straight-chain alkyl groups having 1 to 30 carbon atoms, halogenated branched alkyl groups having 3-30 carbon atoms, one or more alkoxyalkyl groups linked through an at least divalent linker to the pyrrole nitrogen, an optionally substituted aryl, an optionally substituted arylalkyl, and an optionally substituted heterocyclic group.

2. The compound or salt of claim 1, wherein both $R_3$ are hydrogen.

3. The compound or salt of claim 1, wherein $R_3$ is an amine protecting group.

4. The compound or salt thereof of claim 3, wherein $R_3$ is —CO—PR and PR is an OR' group where R' is a straight-chain or branched chain unsubstituted alkyl, an optionally substituted aryl group, an optionally substituted arylakyl group, a halogenated alkyl group having 1 to 12 carbon atoms, or an optionally substituted sulfonylaryl group (—SO$_2$-Aryl).

5. The compound or salt of claim 4, wherein R' is a t-butyl group (BOC), a fluorenylmethyl (FMOC) group, an optionally-substituted benzyl group (CBz), a trifluoromethyl group, a trichloroethyl group (Troc), or a sulfonylaryl group (—SO$_2$-Aryl).

6. The compound or salt of claim 1, wherein $R_3$ is an alkoxyalkyl group linked to the pyrrolic nitrogen by an at least divalent linker.

7. The compound or salt of claim 6, wherein $R_3$ is a group selected from:

$R_G$—O—(—($CH_2$)$_p$—O—)$_q$—$R_H$—Y—, and $R_G$—O—(—(CHR$_I$)$_p$—O—)$_q$—$R_H$—Y— where:

p is an integer 2-4, q is an integer 1-30, $R_G$ is a C1-C4 alkyl, $R_H$ is a C1-C4 alkylene, $R_I$ is independently a hydrogen or a C1-C3 alkyl and Y is —CO—, —O—CO—, or —NH—CO—.

8. The compound or salt of claim 1, wherein $R_3$ is an optionally substituted aryl, an optionally substituted arylalkyl, and an optionally substituted heterocyclic group.

9. The compound or salt of claim 1, wherein $R_3$ is a 5- or 6-member saturated heterocyclic group or a heteroaryl group having 1 or 2 heteroatoms in the ring selected from N, O and S.

10. The compound or salt of claim 1, wherein $R_1$ and $R_2$ are independently selected from a straight-chain alkyl having 3 to 9 carbon atoms or branched-chain alkyl having 3 to 10 carbon atoms.

11. The compound or salt of claim 1, wherein $R_1$ and $R_2$ are selected from branched alkyl groups of formula —C(Ra)(Rb), where Ra and Rb are, independently, alkyl groups having 2-10 carbon atoms.

12. An electronic device employing an electron acceptor, wherein the electron acceptor is one or more compounds or salts of claim 1.

13. The device of claim 12, which is an organic solar cell, an organic thin film transistor or a redox flow battery.

14. A film of a compound or salt of claim 1, wherein both $R^3$ are hydrogen.

15. A method for making a film of a selected compound or salt of claim 1, wherein both $R_3$ are hydrogen which comprises:

preparing a solution of a corresponding compound or salt of said selected compound or salt, wherein both $R_3$ are amine protecting groups, in an organic solvent;

preparing a film of the corresponding compound from said solution; and removing the amine protecting groups from the corresponding compound of said film to form the film of the compound wherein both $R_3$ are hydrogen.

16. A polyimide polymer prepared by copolymerization of a compound or salt of claim 1, where both $R_3$ are hydrogen, with a dibromoaryl or a dibromoalkyl compound.

17. The compound or salt of claim 1, wherein both $R_3$ are hydrogen and wherein each of $R_1$ and $R_2$ are pent-3-yl groups.

18. The compound or salt of claim 1, wherein each $R_3$ is independently selected from hydrogen, halogenated straight-chain alkyl groups having 1 to 30 carbon atoms, halogenated branched alkyl groups having 3-30 carbon atoms, one or more alkoxyalkyl groups linked through an at least divalent linker to the pyrrole nitrogen, an optionally substituted aryl, and an optionally substituted arylalkyl, an optionally substituted heterocyclic group.

19. The compound or salt of claim 1, wherein each $R_3$ is independently selected from hydrogen, halogenated straight-chain alkyl groups having 1 to 30 carbon atoms, halogenated branched alkyl groups having 3-30 carbon atoms, an optionally substituted aryl, an optionally substituted arylalkyl, and an optionally substituted heterocyclic group.

20. The compound or salt of claim 1, wherein the optionally substituted heterocyclic group is an optionally substituted heteroaryl group.

21. The compound or salt of claim 1, compound or salt of claim 1, wherein both $R_3$ are hydrogen and wherein $R_1$ and $R_2$ are selected from branched alkyl groups of formula —C(Ra)(Rb), where Ra and Rb are, independently, alkyl groups having 2-10 carbon atoms.

* * * * *